United States Patent
Cornwell et al.

(10) Patent No.: US 8,865,869 B2
(45) Date of Patent: Oct. 21, 2014

(54) COLLAGEN AND FIBRIN MICROTHREADS IN A DISCRETE THREAD MODEL OF IN VITRO ACL SCAFFOLD REGENERATION

(75) Inventors: Kevin G. Cornwell, Holliston, MA (US); George D. Pins, Holden, MA (US); Kristen Billiar, Worcester, MA (US)

(73) Assignee: Worcester Polytechnic Institute, Worcester, MA (US)

(*) Notice: Subject to any disclaimer, the term of this patent is extended or adjusted under 35 U.S.C. 154(b) by 1218 days.

(21) Appl. No.: 12/293,771

(22) PCT Filed: Mar. 15, 2007

(86) PCT No.: PCT/US2007/006637
§ 371 (c)(1),
(2), (4) Date: Nov. 1, 2010

(87) PCT Pub. No.: WO2007/109137
PCT Pub. Date: Sep. 27, 2007

(65) Prior Publication Data
US 2011/0034388 A1    Feb. 10, 2011

Related U.S. Application Data

(60) Provisional application No. 60/783,949, filed on Mar. 20, 2006.

(51) Int. Cl.
*A61K 35/14* (2006.01)
*C07K 14/00* (2006.01)
*A61L 31/04* (2006.01)
*A61L 27/22* (2006.01)

(52) U.S. Cl.
CPC .............. *A61L 27/225* (2013.01); *A61L 31/046* (2013.01)
USPC .......................................... 530/382; 514/13.6

(58) Field of Classification Search
CPC ........... D01F 8/10; D01F 8/16; A61L 27/225; A61K 35/14; C07K 14/00
See application file for complete search history.

(56) References Cited

U.S. PATENT DOCUMENTS

| | | | |
|---|---|---|---|
| 4,001,459 A | 1/1977 | Kim et al. | |
| 4,683,142 A | 7/1987 | Zimmermann et al. | |
| 4,874,368 A | 10/1989 | Miller et al. | |
| 6,054,122 A * | 4/2000 | MacPhee et al. | 424/94.4 |
| 6,331,422 B1 * | 12/2001 | Hubbell et al. | 435/193 |
| 6,352,710 B2 | 3/2002 | Sawhney et al. | |
| 6,552,172 B2 * | 4/2003 | Marx et al. | 530/382 |
| 6,749,617 B1 | 6/2004 | Palasis et al. | |
| 6,955,681 B2 | 10/2005 | Evans et al. | |
| 7,084,082 B1 | 8/2006 | Shimizu | |
| 7,759,082 B2 | 7/2010 | Bowlin et al. | |
| 2001/0045177 A1 | 11/2001 | Harvey et al. | |
| 2002/0042128 A1 * | 4/2002 | Bowlin et al. | 435/366 |
| 2002/0055759 A1 | 5/2002 | Shibuya | |
| 2002/0168398 A1 * | 11/2002 | Delmotte | 424/443 |
| 2003/0021777 A1 * | 1/2003 | Harris et al. | 424/94.64 |
| 2005/0125035 A1 | 6/2005 | Cichocki | |
| 2006/0029578 A1 | 2/2006 | Hoemann et al. | |

FOREIGN PATENT DOCUMENTS

EP    0463887 A2    1/1992

OTHER PUBLICATIONS

Hocking et. al. Extracellular matrix Fibronectin Mechanically couples Skeletal Muscle Contraction with Local Vasodilation, Integrative Physiology, Circulation Research, p. 372-370, (2008).*
Hocking et al., "Extracellular Matrix Fibronectin Mechanically Couples Skeletal Muscle Contraction With Local Vasodilation," Circulation Research, vol. 102, pp. 372-379, 2008.
Gui et al., "Identification of the Heparin-binding Determinants with Fibronectin Repeat III$_1$," Journal of Biological Chemistry, vol. 281, No. 46, pp. 34816-34825, Nov. 17, 2006.
International Preliminary Report on Patentability for PCT/US2007/006637 dated Sep. 23, 2008.
International Preliminary Report on Patentability for PCT/US2008/057928 dated Sep. 22, 2009.
International Search Report for PCT/US2011/028909 mailed Nov. 24, 2011.

* cited by examiner

*Primary Examiner* — James H Alstrum Acevedo
*Assistant Examiner* — Jeanette Lieb

(57) ABSTRACT

Compositions that include fibrin microthreads are provided. The compositions can include one or more therapeutic agents including cytokines and interleukins, extracellular matrix proteins and/or biologically active fragments thereof (e.g., RGD-containing peptides), hormones, vitamins, nucleic acids, chemotherapeutics, antibiotics, and cells. Also provided are methods of making compositions that include fibrin microthreads. Also provided are methods for using the compositions to repair or ameliorate damaged or defective organs or tissues.

28 Claims, 5 Drawing Sheets

COLLAGEN AND FIBRIN MICROTHREADS IN A DISCRETE THREAD MODEL OF IN VITRO ACL SCAFFOLD REGENERATION

CROSS-REFERENCE TO RELATED APPLICATIONS

This application is the U.S. national stage of international patent application PCT/US2007/006637, filed Mar. 15, 2007, which claims priority to U.S. Provisional Application No. 60/783,949, filed Mar. 20, 2006, each of which is hereby incorporated by reference in its entirety.

TECHNICAL FIELD

This invention relates to tissue engineering, and more particularly to materials that can be implanted in or grafted to a vertebrate subject for repair or amelioration of damaged or defective tissue.

BACKGROUND

Multicellular organisms, including mammals, are made up of tissues, that is, organized aggregates of specialized groups of cells of similar form and function. When tissues become damaged, an ordered series of physiological events must take place in a timely fashion for successful tissue regeneration to occur. The first events, termed the inflammatory phase, include blood clotting as well as the arrival at the wound site of cells that remove bacteria, debris and damaged tissue. Later, circulating stem cells migrate to the wound site and differentiate into tissue-specific cell types. Finally, the differentiated cells begin to produce and deposit new extracellular matrix, a complex assemblage of proteins and carbohydrates that provides support and anchorage for cells.

Successful repair of defective or damaged tissue depends, in part, on providing conditions that allow for appropriate cellular regeneration and that minimize the likelihood of infection during the repair process.

SUMMARY

The present invention is based, in part, on our discovery of compositions and methods that can be used to repair an organ or tissue, including those damaged by trauma or illness and/or those defective at birth. The damaged or defective organs or tissues include those affected by a wide range of medical conditions (e.g., traumatic injuries such as puncture wounds, burns, lacerations, and contusions; congenital malformations such as cleft palate and other facial malformations, genital organ malformations and/or urinary track malformations (e.g., hypospadias), limb malformations, and neural tube defects; and tissue loss, malfunction, or malformation resulting from an infection (e.g. cardiac valve damage or tissue wasting) or surgical procedure (e.g., oncologic resections)). The present compositions and methods can also be used to repair connective tissue such as injured tendons, ligaments, cartilage, and bone.

The compositions can include fibrin (e.g., fibrin microthreads), the structure of which provides a scaffold for tissue growth (e.g., cell-mediated tissue growth and regeneration). Fibrin microthreads can be assembled into hierarchically organized structures such as woven fabrics or ropes of variable size, shape, and character, which may be used alone or in conjunction with other tissue repair materials such as woven or non-woven meshes, pins, screws, plates, patches, filaments, and natural or mechanical valves. The microthreads may be present, for example, as a reinforcing element. The mechanical properties, surface chemistries and porosities of the microthreads can be varied and controlled to direct, alter, and/or facilitate multidimensional cellular alignment and tissue regeneration. The compositions, whether used alone or in combination with another repair substance or device can be shaped in the form of a mesh, dressing, gauze, web, film, patch, sheath or graft for application to or implantation in tissue in need of repair. For example, the assembled microthreads, whether used alone or in combination with another repair substance or device can be applied to damaged connective tissue (e.g., a torn ligament or tendon), defective heart valves, or damaged skin (e.g., at a biopsy site or site of some other wound).

The fibrin microthreads and the structures fabricated from them can also include a variety of types of therapeutic agents. For example, the fibrin microthreads and structures fabricated from them can include growth factors including cytokines and interleukins, extracellular matrix proteins and/or biologically active fragments thereof (e.g., RGD-containing peptides), hormones, vitamins, nucleic acids, chemotherapeutics, antibiotics, and cells. The therapeutic agents can be incorporated singly or in combination into the fibrin microthreads can be adsorbed to the surface of the fibrin microthreads.

Regardless of the precise formulation or configuration, the fibrin microthreads can include filaments of a polymerized fibrin (e.g., human fibrin), which is a serum glycoprotein well studied for its involvement in blood clotting and wound healing. The microthreads can be generally cylindrical in shape with a diameter of less than about 500 µm (e.g., less than about 400 µm, 300 µm, 250 µm, 200 µm, 150 µm, 100 µm, or 50 µm) and more than about 10 µm (e.g., more than about 15 µm, 20 µm, 25 µm, 30 µm, or 40 µm). The polymerized fibrin can include fibrin monomers organized in a staggered overlapping fashion through non-covalent, electrostatic interactions.

Unless the context indicates otherwise, we use the terms "fibrin" and its precursor, "fibrinogen" in their conventional sense to refer to large hexameric glycoproteins composed of pairs of three different subunit polypeptides; multiple isoforms and sequence variants have been identified for the subunits and the sequences are available, if required, to one of ordinary skill in the art. The compositions described herein include fibrin and/or one or more biologically active variants thereof, including any naturally occurring isoform of a fibrin subunit. A polypeptide that has a sequence that differs to a certain limited extent from a sequence that is found in a naturally occurring fibrin subunit polypeptide and that retains the ability to function (e.g., retains sufficient activity to be used for one or more of the purposes described herein) is a biologically active variant of a fibrin polypeptide. We tend to use the terms "fibrin" and "fibrinogen" to refer to the hexameric glycoproteins, and we tend to use the terms "polypeptide" and "peptide" when referring to individual subunits or fragments thereof (i.e., to fragments of fibrin or fibrinogen) and biologically active variants thereof. Because the polypeptides or peptides can have a sequence that is identical to a sequence found in fibrin or fibrinogen, we may characterize the polypeptides or peptides as being derived from fibrin or fibrinogen.

A biologically active variant of a fibrin polypeptide can include, for example, an amino acid sequence that differs from a reference sequence of a fibrin polypeptide by virtue of containing one or more conservative amino acid substitutions, non-conservative amino acid substitutions, additions, and/or deletions. Biologically active variants can also encompass fibrin polypeptides that include non-standard amino acids, for example, amino acids having the D-configuration instead of the standard L-configuration, as well as those amino acids that can be formed by modifications of standard amino acids (e.g. pyrrolysine or selenocysteine). For ease of reading, we do not repeat the phrase "and/or biologically active variants thereof" after every reference to fibrin or a fibrin polypeptide subunit. It is to be understood that where a form of fibrin or a fibrin polypeptide is useful, a variant of the polypeptide that has comparable biological activity (e.g., sufficient activity to be used for one or more of the purposes described herein (e.g., for the purpose for which one would have used a fibrin polypeptide)) is also useful, for example, fibrin analogs, precursors or active fragments thereof, fibrinogen analogs, precursors or active fragments thereof.

In other embodiments, the fibrin microthreads can include one or more therapeutic agents. We use the term "agent" to refer broadly to any substance that affects a target molecule or tissue in a clinically beneficial way (e.g., to promote migration and/or growth of regenerative cells into damaged tissue). The specific agents included can vary and may be selected according to the particular tissue type in need of repair and the nature of the damage or injury necessitating the repair. For example, we may refer to growth factors as "agents". Growth factors can be polypeptides or fragments of polypeptides that retain the bioactive properties of the native growth factor. Useful growth factors can include for example, vascular endothelial cell growth factor (VEGF, e.g., VEGF A, B, C, and D), insulin-like growth factors I and II (IGF-I and IGF-II), interferons (e.g., interferon $\alpha$, $\beta$, or $\gamma$) stem cell factor (SCF) or another cytokine that promotes the differentiation of hematopoietic stem cells into other types of cells.

The therapeutic agent can also be an extracellular matrix (ECM) protein, for example, a collagenous (e.g., collagen 1, collagen 4) or non-collagenous ECM protein (e.g., elastin, laminin, decorin, proteoglycan, aggrecan). Blood and serum proteins can also be included, for example, plasminogen activator inhibitor, fibronectin, albumin, thrombospondin, von Willebrand factor and fibulin. Other useful agents can include nucleic acids or nucleic acid-based entities such as antisense oligonucleotides or nucleic acids that mediate RNAi, as well as the vectors used for delivery. Growth factors that are proteins may delivered to a subject by administering expression vectors (e.g., plasmids or viral vectors) containing nucleic acid sequences encoding any one or more of those factors.

In another embodiment, the therapeutic agent can be a cell. Viable cells, for example, embryonic stem cells, mesenchymal stem cells, monocytes, hematopoetic stem cells, or fibroblasts, can assist in repopulating damaged or defective tissue. Cells can also serve as sources for synthesis and/or secretion of growth factors in situ, e.g., cells that have been transfected or transduced with genes encoding growth factors or irradiated tumor cells that secrete high levels of particular growth factors such as GM-CSF.

A therapeutic agent can also be a small molecule. Small molecule drugs can be incorporated into the fibrin microthreads to facilitate localized drug delivery. Incorporation of antimicrobial agents into the fibrin microthreads can provide local high concentrations of antibiotics, thus minimizing the risk of adverse effects associated with long term high systemic doses. An antimicrobial agent can be an antibiotic, for example, an aminoglycoside, a cephalosporin, a macrolide, a penicillin, a peptide, a quinolone, a sulfonamide, or a tetracycline. Other antimicrobial agents, e.g., antifungal agents and antiviral agents can also be included in the fibrin microthreads. A small molecule drug can also be a chemotherapeutic agent. Incorporation of anticancer agents into the biocompatible tissue repair compositions can provide local high concentrations of chemotherapy, thus mitigating the toxicity associated with long term high systemic doses. A chemotherapeutic agent can be for example, an alkylating agents, an anthracycline, a cycloskeletal disruptor, a topoisomerase inhibitor, a nucleotide analogue, a peptide, a platinum-based agent, a retinoid, or a vinca alkaloid.

In another embodiment, the fibrin microthreads can include a diagnostic agent, i.e., an agent that is useful for monitoring the condition of the implanted compositions within the body of the host in a non-invasive manner. Diagnostic agents can include, without limitation, for example, contrast agents, fluorescently labeled microspheres, quantum dots or iron oxides.

Also featured are methods of making fibrin microthreads. During the normal course of blood coagulation, the enzyme thrombin cleaves small peptides from the $A\alpha$ and $B\beta$ chains of fibrinogen to generate the fibrin monomer. The fibrin microthreads are formed by coextruding a solution of fibrinogen, the fibrin precursor, with one or more molecules capable of forming fibrin, under conditions suitable for fibrin formation, into an aqueous buffered medium, incubating the extruded solution until filament formation is observed, and then drying the filaments. During the extrusion process, the fibrinogen is cleaved to generate fibrin monomers that self-assemble in situ to form filaments.

Any form of fibrinogen that retains the ability to function (e.g., retains sufficient activity to be used for one or more of the purposes described herein) may be used in the manufacture of the fibrin microthreads. The source of the fibrin/fibrinogen can vary, that is, the fibrin/fibrinogen may be from any mammal provided that the fibrin retains the ability to function (e.g., retains sufficient activity to be used for one or more of the purposes described herein). Thus, the fibrinogen may be obtained from any of a wide range of species, e.g., humans, non-human primates (e.g., monkeys), horses, cattle, pigs, sheep, rabbits, guinea pigs, hamsters, rats, and mice. The fibrinogen may be obtained from the host's own tissue or an allogeneic donor.

The fibrinogen may be partially or substantially pure. The term "substantially pure" with respect to fibrinogen refers to fibrinogen that has been separated from cellular components with which it is naturally accompanied, such that it is at least 60% (e.g., 70%, 80%, 90%, 95%, or 99%), by weight, free from polypeptides and other naturally-occurring organic molecules with which it is naturally associated.

Any enzyme that cleaves fibrinogen in a manner that insures that the resulting fibrin monomers retain the ability to function (e.g., retains sufficient activity to be used for one or more of the purposes described herein) may be used in the manufacture of the fibrin microthreads. Examples of useful enzymes include, but are not limited to, thrombin, active fragments of thrombin, thrombin analogues, reptilase, batroxobin, and a variety of other snake venom enzymes.

Fibrin formation may be initiated by mixing the fibrinogen and the enzyme (e.g., thrombin) simultaneously with or immediately prior to extrusion of the solution through an orifice. The coextrusion step may be repeated one or more times to produce a multifilament fibrin microthread scaffold. The fibrin microthreads may also be covalently cross-linked.

The fibrin microthreads may be assembled in a variety of ways. For example, they may be woven, braided, or otherwise intertwined to generate a variety of patches or grafts for tissue repair. The size and shape of the resulting material will vary according to the nature of the repair that is contemplated. Examples of repair procedures include, but are not limited to repair of vascular valves; provision of vascular grafts; repair of connective tissues (e.g., tendon, cartilage, or ligament) with or without accompanying muscle or bone repair; provision of a vascular scaffold or support; wound care; hernia patch; nerve repair; and suturing. The fibrin microthreads may also be combined with or incorporated into other tissue repair materials, for example, collagen-based compositions, synthetic polymers or bioresorbable materials.

The methods of the invention include methods for treating a subject (e.g., a human patient) with a tissue in need of repair. The repair can include tissue augmentation, the replacement or all or part of a tissue, or restoration or improvement in tissue function to any beneficial extent. These methods can include the steps of a) identifying a subject who has or is likely to have tissue in need of repair; and b) providing to the subject a composition including fibrin microthreads. The compositions can be administered to a subject in a variety of ways. The fibrin microthreads and compositions including fibrin microthreads can be applied to an individual in need of treatment using techniques known to those of skill in the art. For example, the biocompatible tissue repair compositions can be: (a) wrapped around a tissue that is damaged or that contains a defect; (b) placed on the surface of a tissue that is damaged or has a defect; and/or (c) rolled up and inserted into a cavity, gap, or space in the tissue. One or more (e.g., one, two, three, four, five, six, seven, eight, nine, ten, 12, 14, 16, 18, 20, 25, 30, or more) such compositions, stacked or adjacent to each other, can be used at any particular site or at adjacent sites. The compositions can be held in place by, for example, sutures, staples, tacks, or tissue glues or sealants known in the art. The patient's own tissue (e.g., a flap of tissue at the site or a harvested synovial membrane) or a synthetic membrane may also be used to help secure the repair compositions. Alternatively, if, for example, packed sufficiently tightly into a defect or cavity, they may need no securing device. The compositions can be administered along with or in addition to standard treatments for particular tissue repairs (e.g., drug therapy, immunotherapy; or surgery).

As noted above, the compositions described herein can be used to treat any of a wide range of disorders in which tissue repair is needed. Thus, the compositions can be used to repair soft tissues in many different organ systems. These organ systems can include, but are not limited to, the muscular system, the genitourinary system, the gastroenterological system, the integumentary system, the circulatory system and the respiratory system. Examples include, but are not limited to, topical wound care; skin grafts; dural patches; bed sores; ulcers, including diabetic ulcers; cuts; abrasions; fascial replacements; surgical applications such as biological suture material; matrix for micro-organ production; nerve guide for nerve repair as a nerve replacement when combined with neurogenic stem cells; as a scaffold for introducing or reintroducing cells into the body.

The compositions described herein can also be assembled in kits, together with instructions for use. For example, the kits can include measured amounts of fibrin microthreads or a composition fabricated from fibrin microthreads and packaging materials.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
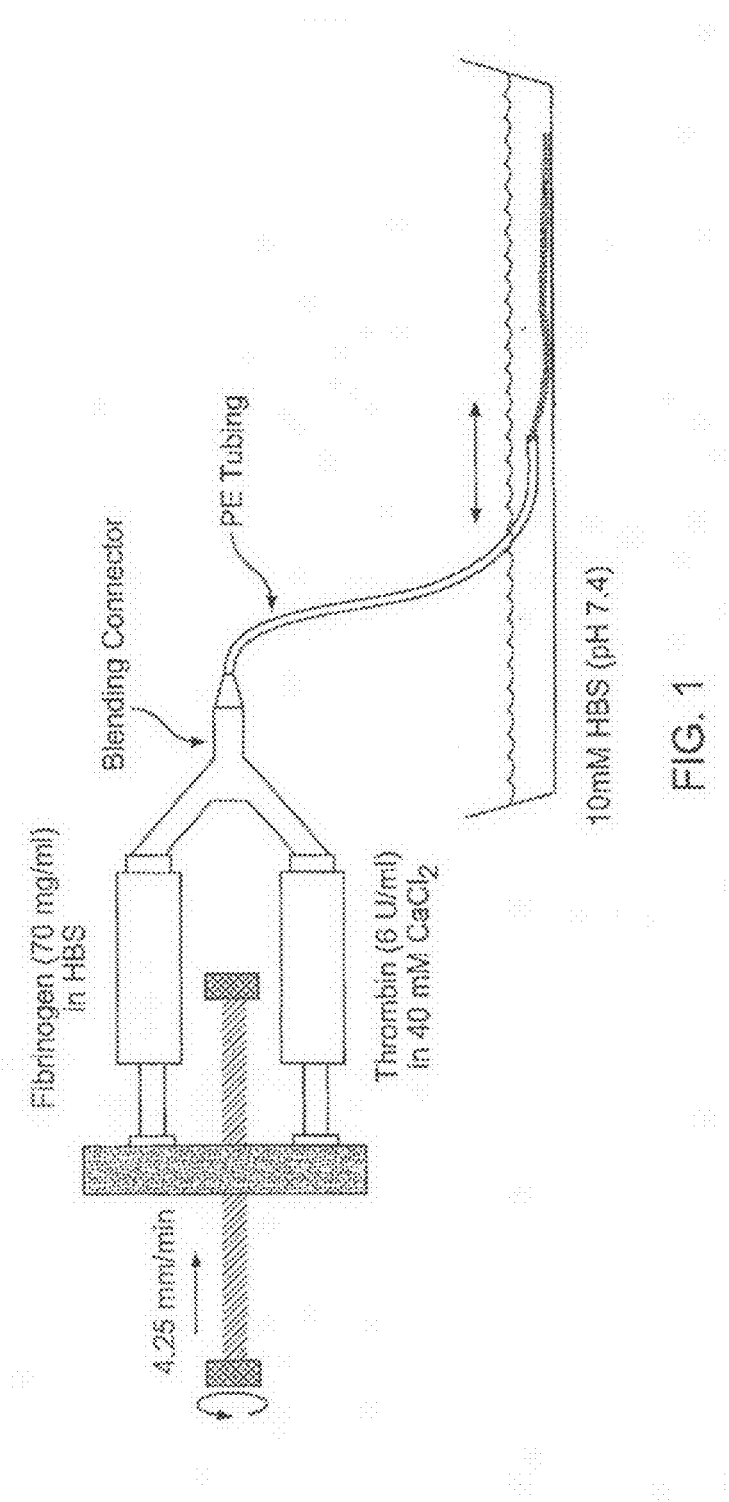
FIG. 1 is a schematic drawing of the coextrusion system.

During the initial phase of wound healing, the formation of a provisional matrix precedes a series of cell-mediated events that guide tissue repair and regeneration. The provisional matrix is assembled from a plasma derived protein, fibrin, in conjunction with other extracellular matrix proteins including fibronectin and vitronectin. This fibrin matrix serves as a reservoir for cytokines and acts as a scaffold that directs the recruitment of cells from the wound margin into the injury site. Furthermore, this provisional matrix facilitates tissue regeneration by promoting migration, attachment, and proliferation of cells while directing cell signaling through integrin based mechanisms.

Disclosed herein are materials and methods for the production and use compositions that can be implanted into or grafted on to a damaged or defective tissue to facilitate repair of the damaged or defective organ or tissue. More specifically, the composition comprises fibrin microthreads, i.e., filaments of polymerized fibrin that are generally cylindrical in shape with a diameter of less than about 100 μM. In some embodiments, the fibrin microthreads can include one or more therapeutic agents, for example, growth factors, extracellular matrix proteins, hormones, vitamins, chemotherapeutics, antibiotics and cells. Alternatively or in addition, the fibrin microthreads can include other polymers.

Compositions

Provided herein is a method of making a fibrin microthread composition, the method including providing fibrinogen and a sufficient amount of a molecule capable of forming fibrin from the fibrinogen; and extruding a mixture of the fibrinogen and the molecule through an orifice into a medium thereby producing a fibrin microthread. The molecule is a protease, for example, thrombin. The medium is a buffered solution having a pH of about 6.0 to about 8.0; a suitable pH is about 7.4. The fibrin microthreads are formed by coextruding a solution of fibrinogen, the fibrin precursor, with one or more molecules capable of forming fibrin, under conditions suitable for fibrin formation, into an aqueous buffered medium, incubating the extruded solution until filament formation is observed, and then drying the filaments. During the extrusion process, the fibrinogen is cleaved to generate fibrin monomers which self-assemble in situ to form filaments.

Polypeptides

The terms "polypeptide" and "peptide" are used herein to refer to a compound of two or more subunit amino acids, amino acid analogs, or other peptidomimetics, regardless of post-translational modification (e.g., amidation, phosphorylation or glycosylation). The subunits can be linked by peptide bonds or other bonds such as, for example, ester or ether bonds. The term "amino acid" refers to natural and/or unnatural or synthetic amino acids, which may, as noted above, be D- or L-form optical isomers. Full-length proteins, analogs, mutants, and fragments thereof are encompassed by this definition.

Fibrinogen

The fibrin component of the fibrin microthreads is a proteolytic cleavage product of fibrinogen. Fibrinogen, a soluble protein typically present in human blood plasma at concentrations between about 2.5 and 3.0 g/L, is intimately involved in a number of physiological processes including hemostasis, angiogenesis, inflammation and wound healing. Fibrinogen is 340,000 Da hexameric glycoprotein composed of pairs of three different subunit polypeptides, Aα, Bβ, and γ, linked together by a total of 29 disulfide bonds. During the normal course of blood coagulation, the enzyme thrombin cleaves small peptides from the Aα and Bβ chains of fibrinogen to generate the insoluble fibrin monomer. The fibrin monomers self-assemble in a staggered overlapping fashion through non-covalent, electrostatic interactions to form protofibrils; the protofibrils further assemble laterally into thicker fibers that ultimately intertwine to produce a clot.

Fibrinogen is expressed primarily in the liver, although low levels of extrahepatic synthesis have been reported for other tissues, including bone marrow, brain; lung and intestines. The thrombin catalyzed conversion of fibrinogen to fibrin is common to all extant vertebrates; accordingly, the amino acid sequence of fibrinogen is highly conserved evolutionarily. Each polypeptide subunit is the product of a separate but closely linked gene; multiple isoforms and sequence variants have been identified for the subunits. Amino acid sequences for the fibrinogen subunits are in the public domain. The fibrinogen Aα polypeptide is also known as fibrinogen α chain polypeptide; fibrinogen a chain precursor; Fib2; MGC119422; MGC119423; and MGC119425. The fibrinogen Bβ polypeptide is also known as fibrinogen β chain polypeptide; fibrinogen β chain preproprotein; MGC104327; and MGC120405 and the fibrinogen γ polypeptide is also known as fibrinogen γ chain polypeptide and fibrinogen γ chain precursor.

Any form of fibrinogen that retains the ability to function (e.g., retains sufficient activity to be used for one or more of the purposes described herein) may be used in the manufacture of the fibrin microthreads. The fibrinogen is human fibrinogen or fibrinogen of a non:human primate, a domesticated animal, or a rodent. The fibrinogen is obtained from a naturally occurring source or is recombinantly produced. All that is required is that the fibrinogen retains the ability to form polymerized fibrin monomers and that the fibrin microthreads prepared from those fibrin monomers retain, or substantially retain, the capacity to support cell attachment and proliferation. The amino acid sequence of fibrinogen subunit polypeptides can be identical to a standard reference sequence in the public domain. As noted, the present invention includes biologically active variants of fibrinogen subunit polypeptides, and these variants can have or can include, for example, an amino acid sequence that differs from a reference fragment of a fibrinogen subunit polypeptide by virtue of containing one or more mutations (e.g., an addition, deletion, or substitution mutation or a combination of such mutations). One or more of the substitution mutations can be a substitution (e.g., a conservative amino acid substitution), with the proviso that at least or about 50% of the amino acid residues of the variant are identical to residues in the corresponding wildtype fragment of a fibrinogen subunit polypeptides. For example, a biologically active variant of a fibrinogen subunit polypeptides can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a fibrinogen subunit polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. Alternatively, any of the components can contain mutations such as deletions, additions, or substitutions. All that is required is that the variant fibrinogen subunit polypeptide have at least 5% (e.g., 10%, 20%, 30%, 40%, 50%, 60%, 70%, 80%, 90%, 95%, 99%, 100%, or even more) of the ability of the variant fibrinogen subunit polypeptide containing only the reference sequences to retains the ability to form polymerized fibrin monomers and that the fibrin microthreads prepared from those fibrin monomers retain, or substantially retain, the capacity to support cell attachment and proliferation.

The fibrinogen may be obtained from any of a wide range of species. It is not necessary that the fibrinogen be from a species that is identical to the host, but should simply be amenable to being remodeled by invading or infiltrating cells such as differentiated cells of the relevant host tissue, stem cells such as mesenchymal stem cells, or progenitor cells. The fibrinogen useful for the invention can optionally be made from a recipient's own tissue. Furthermore; while the fibrinogen will generally have been made from one or more individuals of the same species as the recipient of the fibrin microthreads, this is not necessarily the case. Thus, for example, the fibrinogen can be derived from bovine tissue and be used to make fibrin microthreads that can be implanted in a human patient. Species that can serve as recipients of fibrin microthreads and fibrinogen donors for the production of of fibrin microthreads can include, without limitation, mammals, such as humans, non-human primates (e.g., monkeys, baboons, or chimpanzees), pigs, cows, horses, goats, sheep, dogs, cats, rabbits, guinea pigs, gerbils, hamsters, rats, or mice.

The fibrinogen may be partially or substantially pure. The term "substantially pure" with respect to fibrinogen refers to fibrinogen that has been separated from cellular components by which it is naturally accompanied, such that it is at least 60% (e.g., 70%, 80%, 90%, 95%, or 99%), by weight, free from polypeptides and naturally-occurring organic molecules with which it is naturally associated. In general, a substantially pure polypeptide will yield a single major band on a non-reducing polyacrylamide gel. A substantially pure polypeptide provided herein can be obtained by, for example, extraction from a natural source (e.g., blood or blood plasma from human or animal sources; e.g., non-human primates (e.g., monkeys, baboons, or chimpanzees), pigs, cows, horses, goats, sheep, dogs, cats, rabbits, guinea pigs, gerbils, hamsters, rats, or mice), chemical synthesis, or by recombinant production in a host cell.

The fibrinogen can include post-translational modifications, i.e., chemical modification of the polypeptide after its synthesis. Chemical modifications can be naturally occurring modifications made in vivo following translation of the mRNA encoding the fibrinogen polypeptide subunits or synthetic modifications made in vitro. A polypeptide can include one or more post-translational modifications, in any combination of naturally occurring, i.e., in vivo, and synthetic modifications made in vitro. Examples of post-translational modifications glycosylation, e.g., addition of a glycosyl group to either asparagine, hydroxylysine, serine or threonine residues to generate a glycoprotein or glycopeptides. Glycosylation is typically classified based on the amino acid through which the saccharide linkage occurs and can include: N-linked glycosylation to the amide nitrogen of asparagines side chains, O-linked glycosylation to the hydroxyl oxygen of serine and threonine side chains, and C-mannosylation. Other examples of pot-translation modification include, but are not limited to, acetylation, e.g., the addition of an acetyl group, typically at the N-terminus of a polypeptide; alkylation, e.g., the addition of an alkyl group; isoprenylation, e.g., the addition of an isoprenoid group; lipoylation, e.g. attachment of a lipoate moeity; phosphorylation, e.g., addition of a phosphate group to serine, tyrosine, threonine or histidine; and biotinylation, e.g., acylation of lysine or other reactive amino acid residues with a biotin molecule.

Fibrinogen can be purified using any standard method know to those of skill in the art including, without limitation, methods based on fibrinogen's low solubility in various solvents, its isoelectric point, fractionation, centrifugation, and chromatography, e.g., gel filtration, ion exchange chromatography, reverse-phase HPLC and immunoaffinity purification. Partially or substantially purified fibrinogen can also be obtained from commercial sources, including for example Sigma, St. Louis, Mo.; Hematologic Technologies, Inc. Essex Junction, Vt.; Aniara Corp. Mason, Ohio.

Fibrinogen can also be produced by recombinant DNA techniques. Nucleic acid segments encoding the fibrinogen polypeptide subunits can be operably linked in a vector that includes the requisite regulatory elements, e.g., promoter sequences, transcription initiation sequences, and enhancer sequences, for expression in prokaryotic or eukaryotic cells. Methods well known to those skilled in the art can be used to construct expression vectors containing relevant coding sequences and appropriate transcriptional/translational control signals. Alternatively, suitable vector systems can be purchased from commercial sources.

Nucleic acid segments encoding the fibrinogen polypeptide subunits are readily available in the public domain. The terms "nucleic acid" and "polynucleotide" are used interchangeably herein, and these terms refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. The nucleic acid molecules can be synthesized (for example, by phosphoramidite based synthesis) or obtained from a biological cell, such as the cell of a mammal. The nucleic acids can be those of mammal, e.g., humans, a non-human primates, cattle, horses, pigs, sheep, goats, dogs, cats, rabbits, guinea pigs, hamsters, rats, or mice.

An "isolated" nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids disclosed herein also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence can be aligned to one or more subject nucleic acid or amino acid sequences using the computer program ClustalW (version 1.83, default parameters), which allows alignments of nucleic acid or protein sequences to be carried out across their entire length (global alignment). Chenna et al., Nucleic Acids Res., 31(13):3497-500 (2003). ClustalW can be run, for example, at the Baylor College of Medicine Search Launcher Site (searchlauncher.bcm.tmc.edu/multi-align/multi-align.html) and at the European Bioinformatics Institute site on the World Wide Web (ebi.ac.uk/clustalw).

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid.

A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Vectors typically contain one or more regulatory regions. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

The vectors also can include, for example, origins of replication, scaffold attachment regions (SARs), and/or markers. A marker gene can confer a selectable phenotype, e.g., antibiotic resistance, on a cell. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The expression vectors disclosed herein containing the above described coding can be used, for example, to transfect or transduce either prokaryotic (e.g., bacteria) cells or eukaryotic cells (e.g., yeast, insect, or mammalian) cells. Such cells can then be used, for example, for large or small scale in vitro production of the fibrinogen polypeptides by methods known in the art. In essence, such methods involve culturing the cells under conditions which maximize production of the fusion protein and isolating the fusion protein from the cells or from the culture medium.

Therapeutic Agents

Therapeutic agents that aid tissue regeneration can be included in the fibrin microthread compositions. These agents can include growth factors including cytokines and interleukins, extracellular matrix proteins and/or biologically active fragments thereof (e.g., RGD-containing peptides), blood and serum proteins, nucleic acids, hormones, vitamins, chemotherapeutics, antibiotics and cells. These agents can be incorporated into the compositions prior to the compositions being placed in the subject. Alternatively, they can be injected into or applied to the composition already in place in a subject. These agents can be administered singly or in combination. For example, a composition can be used to deliver cells, growth factors and small molecule therapeutics concurrently, or to deliver cells plus growth factors, or cells plus small molecule therapeutics, or growth factors plus small molecule therapeutics.

Growth factors that can be incorporated into the biocompatible tissue repair composition include any of a wide range of cell growth factors, angiogenic factors, differentiation factors, cytokines, hormones, and chemokines known in the art. Growth factors can be polypeptides that include the entire amino acid sequence of a growth factor, a peptide that corresponds to only a segment of the amino acid sequence of the native growth factor, or a peptide that derived from the native sequence that retains the bioactive properties of the native growth factor. The growth factor can be a cytokine or interleukin. Any combination of two or more of the factors can be administered to a subject by any of the means recited below. Examples of relevant factors include vascular endothelial cell growth factors (VEGF) (e.g., VEGF A, B, C, D, and E), platelet-derived growth factor (PDGF), insulin-like growth factor (IGF) I and IGF-II, interferons (IFN) (e.g., IFN-α, β, or γ), fibroblast growth factors (FGF) (e.g., FGF1, FGF-2, FGF-3, FGF-4-FGF-10), epidermal growth factor, keratinocyte growth factor, transforming growth factors (TGF) (e.g., TGFα or β), tumor necrosis factor-α, an interleukin (IL) (e.g., IL-1, IL-2, Il-17-IL-18), Osterix, Hedgehogs (e.g., sonic or desert), SOX9, bone morphogenetic proteins (BMP's), in particular, BMP 2, 4, 6, and (BMP-7 is also called OP-1), parathyroid hormone, calcitonin prostaglandins, or ascorbic acid.

Factors that are proteins can also be delivered to a recipient subject by administering to the subject: (a) expression vectors (e.g., plasmids or viral vectors) containing nucleic acid sequences encoding any one or more of the above factors that are proteins; or (b) cells that have been transfected or transduced (stably or transiently) with such expression vectors. Such transfected or transduced cells will preferably be derived from, or histocompatible with, the recipient. However, it is possible that only short exposure to the factor is required and thus histo-incompatible cells can also be used.

Other useful proteins can include, without limitation, hormonse, an extracellular antibodies, extracellular matrix proteins, and/or biologically active fragments thereof (e.g., RGD-containing peptides) or other blood and serum proteins, e.g., fibronectin, albumin, thrombospondin, van Willebrand factor and fibulin.

Naturally, administration of the agents mentioned above can be single, or multiple (e.g., two, three, four, five, six, seven, eight, nine, 10, 15, 20, 25, 30, 35, 40, 50, 60, 80, 90, 100, or as many as needed). Where multiple, the administrations can be at time intervals readily determinable by one skilled in art. Doses of the various substances and factors will vary greatly according to the species, age, weight, size, and sex of the subject and are also readily determinable by a skilled artisan.

Histocompatible, viable cells can be restored to the biocompatible tissue repair compositions to produce a permanently accepted graft that may be remodeled by the host. Cells can be derived from the intended recipient or an allogeneic donor. Cell types with which the biocompatible tissue repair compositions can be repopulated include, but are not limited to, embryonic stem cells (ESC), adult or embryonic mesenchymal stem cells (MSC), monocytes, hematopoetic stem cells, gingival epithelial cells, endothelial cells, fibroblasts, or periodontal ligament stem cells, prochondroblasts, chondroblasts, chondrocytes, pro-osteoblasts, osteocytes, or osteoclast. Any combination of two or more of these cell types (e.g., two, three, four, five, six, seven, eight, nine, or ten) may be used to repopulate the biocompatible tissue repair composition. Methods for isolating specific cell types are well-known in the art. Donor cells may be used directly after harvest or they can be cultured in vitro using standard tissue culture techniques. Donor cells can be infused or injected into the biocompatible tissue repair composition in situ just prior to placing of the biocompatible tissue repair composition in a mammalian subject. Donor cells can also be cocultured with the biocompatible tissue repair composition using standard tissue culture methods known to those in the art.

Small molecule drugs can also be incorporated into the biocompatible tissue repair composition, thus facilitating localized drug delivery. Long-term systemic administration of antibiotics may only be partially effective against such subclinical infections. Incorporation of antimicrobial agents into the biocompatible tissue repair composition can provide local high concentrations of antibiotics, thus minimizing the risk of adverse effects associated with long term high systemic doses. An antimicrobial agent can be an antibiotic. Examples of antibiotics include, without limitation, any representative classes of antibiotics, e.g., 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B or vancomycin; 6) quinolones, such as ciprofloxacin, levofloxacin, or enoxacin; 7) sulfonamides, such as sulfamethazole, sulfacetimide; or sulfamethoxazole; 8) tetracyclines, such as doxycycline, minocycline or tetracycline; 8) other antibiotics with diverse mechanisms of action such as rifampin, chloramphenicol, or nitrofuratoin. Other antimicrobial agents, e.g., antifungal agents and antiviral agents can also be included in the compositions.

Chemotherapeutic agents can also be included in the compositions. Malignant tumors that occur in soft tissue, including for example, tumors of the esophagus, stomach, colon, bladder are typically treated by tumor resection and systemic administration of anticancer drugs. Incorporation of anticancer agents into the biocompatible tissue repair compositions can provide local high concentrations of chemotherapy, thus mitigating the toxicity associated with long term high systemic doses. Examples of classes of chemotherapeutic agents include, without limitation, 1) alkylating agents, e.g., cyclophosphamide; 2) anthracyclines, e.g., daunorubicin, doxorubicin; 3) cycloskeletal disruptors, e.g., paclitaxel; 4) topoisomerase inhibitors, e.g., etoposide; 5) nucleotide analogues, e.g., azacitidine, fluorouracil, gemcitabine; 6) peptides, e.g., bleomycin; 7) platinum-based agents, e.g., carboplatin, cisplatin; 8) retinoids, e.g., all-trans retinoic acid; and 9) vinca alkaloids, e.g., vinblastine or vincristine.

Preparation of Fibrin Microthread Compositions

The fibrin microthreads provided herein are made by mixing a solution of fibrinogen with a solution of one or more molecules capable of forming fibrin, under conditions suitable for fibrin formation; coextruding the mixture through an orifice into an aqueous buffered medium, incubating the extruded solution until filament formation is observed, and then drying the filaments.

Fibrinogen cleavage can be carried out by any method know to those of skill in the art. The fibrinogen can be suspended in any aqueous medium that is compatible with the activity of the fibrin-forming enzyme e.g., thrombin. Examples of suitable buffer systems include HEPES-buffered saline, tris-buffered saline, phosphate buffered saline, MES, PIPES. Any concentration of fibrinogen that results in fibrin microthread formation can be used. The exact concentration may vary according to extrusion conditions. Suitable concentrations are about 70 mg/mL. "About" indicates that the fibrinogen concentration can vary by up to 10% above or below the recited value.

The thrombin can be suspended in any aqueous medium that is compatible with enzymatic activity. Examples of useful buffer systems include HEPES-buffered saline, tris-buffered saline, phosphate buffered saline, MES, PIPES. The buffer may also include a divalent cation, e.g. $CaCl_2$. Any concentration of thrombin that results in fibrin microthread formation can be used. The exact concentration may vary according to extrusion conditions. Suitable concentrations are about 6 U/mL. "About" indicates that the thrombin concentration can vary by up to 10% above or below the recited value.

It will be appreciated that the concentrations of fibrinogen and thrombin, the pH of the buffers, and the swelling temperature may be adjusted to achieve optimal fibrin microthread formation. For example, fibrinogen from different sources, e.g., different mammalian species or different isoforms of fibrinogen from the same species, may require different cleavage conditions in order to synthesize fibrin microthreads of requisite tensile strength or tissue regeneration properties.

Any apparatus known to those of skill in the art can be used for coextrusion of the fibrinogen and thrombin solutions. A suitable apparatus can include a stabilized crosshead on a threaded rod with a crosshead speed of 4.25 mm/min through a blending applicator tip (Micromedics, Inc., St. Paul, Minn.). The blending applicators can be Luer locked to the two syringes through individual bores and mixed in a needle that is Luer locked to the tip. The fibrinogen and thrombin solutions can combined and extruded through polyethylene tubing (BD, Sparks, Md.) into an aqueous buffered bath.

The rate of coextrusion can vary according to the type of extrusion apparatus that is employed. The rate of coextrusion can be expressed as a "rate ratio", i.e., the ratio of flow velocity/plotter velocity, where flow velocity is the speed with which the fibrin solution emerges from the tubing and plotter velocity is the speed of the extrusion tubing through the aqueous bath. For example, a rate ratio of 2.0 describes extrusion parameters in which the solution flows out of the tubing twice as fast as the tubing tip moves through the aqueous bath. Useful rate ratios for the apparatus described above can range from about 1.5 to about 6.0, e.g., about 1.6, 1.8. 2.0, 2.5, 3.0, 3.5, 4.0, 4.5, 5.0.

The diameter of the tubing, i.e., the orifice from which the solutions are extruded may also vary. For example, the diameter of the orifice has a diameter can range from about 0.2 μm to about 1,000 μM, (e.g., less than about 1000 μm, 500 μm, 250 μm, 200 μm, 150 μm, 100 μm, or 50 μm) and more than about 10 μm (e.g., more than about 15 μm, 20 μm, 25 μm, 30 μm, or 40 μm). The orifice can have a diameter of about 20 μm to about 100 μm. The orifice can have a diameter of about 380 μm. The extruding step is carried out at a temperature between about 25° C. and about 42° C., inclusive.

The nature of the buffer solution, the pH and the temperature of the aqueous bath may also vary. In general, the aqueous bath can be any include any buffer system that is compatible with fibrin polymerization, e.g., HEPES-buffered saline, tris-buffered saline, phosphate buffered saline, MES, PIPES. The pH of the bath can vary from less than about 8.5 (e.g., less than about 8.3, 8.1, 8.0, 7.9, 7.8, 7.7, 7.6, 7.5, 7.4, 7.3, 7.2, 7.1, 7.0, 6.9, 6.8, 6.7) to more than about 5.5 (e.g. more than about 5.7, 5.8, 6.0, 6.1, 6.2, 6.3, 6.4, 6.5, 6.6, 6.7, 6.8). "About" indicates that the pH can vary by up to 0.2 pH units above or below the recited value. Thus, a pH of "about" 7.4, can include, for example, pH 7.2, 7.3, 7.5 or 7.6. The temperature of the bath can be any temperature compatible with fibrin polymerization and can vary from less than about 40° C. (e.g., less than about 38° C., 37° C., 36° C., 35° C., 34° C., 33° C., 32° C., 31° C., 30° C., 29° C., 28° C.) to more than about 18° C. (e.g., more than about 19° C., 20° C., 21° C., 22° C., 23° C., 24° C., 25° C., 26° C., 27° C.).

The incubation step includes features that prevent the extruded solution from adhering or substantially adhering to the surface of the vessel in which the aqueous bath is contained. Any method that is compatible with fibrin polymerization may be used. For example, the vessel can include one or more materials having an extremely low coefficient of friction to provide a non-stick surface, e.g, polytetrafluoroethylene (Teflon®), fluorinated ethylene-propylene (FEP) and perfluoroalkoxy polymer resin (PFA). Alternatively or in addition, the aqueous buffered medium can include one or more surfactants, detergents or emulsifying agents, for example, Pluronic® surfactants (BASF) polyethylene glycol, or tri-ethylene glycol. The appropriate concentration of such reagent will vary according to the nature of the reagent and may be readily determined empirically by one of skill in the art. Alternatively or in addition, the medium is physically agitated.

Formation in the fibrin microthreads in the aqueous bath can typically be observed within a few minutes of the coextrusion process. The incubation step can vary from more than about 1 minute (e.g., 1.5 minutes, 2.0 minutes, 2.5 minutes, 3.0 minutes, 3.5 minutes) to less than about 3.0 hours (e.g. 2.5 hours, 2.0 hours, 1.5 hours, 1.0 hours, 0.5 hours.).

The fibrin microthreads are recovered from the medium and permitted to dry. The fibrin microthreads can be dried by any method known in the art that will result in the 1.0 retention of biological and physical functions of the fibrin microthreads. Drying methods include, without limitation, e.g., air drying, drying in atmosphere of, or under a stream of, inert gas (e.g., nitrogen or argon). The drying temperature may be ambient temperature, e.g., about 25° C. or it can be a temperature that is mildly elevated relative to ambient temperature, e.g., 28° C., 29° C., 30° C., 31° C., 32° C., 33° C., 34° C., 35° C., 36° C., 37° C., 38° C., 39° C., 40° C., 41° C., 42° C., 43° C. or 44° C.

In some embodiments, a fibrin microthread can be chemically cross-linked (e.g. covalently linked) to itself and/or other fibrin microthreads. One suitable method of cross-linking is exposure to ultra-violet (uv) light. Methods for uv cross-linking are well known to those of skill in the art. Levels of uv exposure may vary according to the size and configuration of the fibrin microthreads and can range for example, from a calculated total energy of about 4 to about 100 J/cm$^2$, e.g., about 4.5, 5.0, 8.0, 10.0, 15.0 17.1, 20.0 25.0, 30.0 40.0 50.0 60.0. 70.0 80.0, 90.0, 100.0 J/cm$^2$ Cross-linking can also be carried out using chemical cross-linking agents. Chemical cross-linking agents can be homo-bifunctional (the same chemical reaction takes place at each end of the linker) or hetero-bifunctional (different chemical reactions take place at the ends of the linker). The chemistries available for such linking reactions include, but are not limited to, reactivity with sulfhydryl, amino, carboxyl, diol, aldehyde, ketone, or other reactive groups using electrophilic or nucleophilic chemistries, as well as photochemical cross-linkers using alkyl or aromatic azido or carbonyl radicals. Examples of chemical cross-linking agents include, without limitation, glutaraldehyde, carbodiimides, bisdiazobenzidine, and N-maleimidobenzoyl-N-hydroxysuccinimide ester. Chemical cross-linkers are widely available from commercial sources (e.g., Pierce Biotechnology (Rockford, Ill.); Invitrogen (Carlsbad, Calif.); Sigma-Aldrich (St. Louis, Mo.); and US Biological (Swampscott, Mass.)). Particularly suitable cross-linking reagents include 1-ethyl-3-[3-dimethylaminopropyl]carbodiimide hydrochloride (EDAC), and N-hydroxysulfosuccinimide (NHS). The duration of the cross-linking reaction may vary according to the cross-linking agent that is used, the reaction temperature and the tensile strength desired.

Optionally, the fibrin microthreads can be submitted to treatments to diminish the bioburden. This process is expected to decrease the level of infectious microorganisms within the fibrin microthreads. As used herein, a process used to inactivate or kill "substantially all" microorganisms (e.g., bacteria, fungi (including yeasts), and/or viruses) in the fibrin microthreads is a process that reduces the level of microorganisms in the fibrin microthreads by least 10-fold (e.g., at least: 100-fold; 1,000-fold; $10^4$-fold; $10^5$-fold; $10^6$-fold; $10^7$-fold; $10^8$-fold; $10^9$-fold; or even $10^{10}$-fold) compared to the level in the fibrin microthreads prior to the process. Any standard assay method may be used to determine if the process was successful. These assays can include techniques that directly measure microbial growth, e.g., the culture of swab samples on artificial growth media, or molecular detection methods, such as quantitative PCR.

The fibrin microthreads can be exposed to γ-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm) radiation in order to decrease the level of, or eliminate, viable bacteria and/or fungi and/or infectious viruses. More important than the dose of radiation that the fibrin microthreads is exposed to is the dose absorbed by the fibrin microthreads. While for thicker fibrin microthreads, the dose absorbed and the exposure dose will generally be close, in thinner fibrin microthreads the dose of exposure may be higher than the dose absorbed. In addition, if a particular dose of radiation is administered at a low dose rate over a long period of time (e.g., two to 12 hours), more radiation is absorbed than if it is administered at a high dose rate over a short period of time (e.g., 2 seconds to 30 minutes). One of skill in the art will know how to test for whether, for a particular fibrin microthreads, the dose absorbed is significantly less than the dose to which the fibrin microthreads is exposed and how to account for such a discrepancy in selecting an exposure dose.

The tensile strength of the fibrin microthreads will vary according to size and the methods used for synthesis. Methods for measuring tensile strength are well-known to those of skill in the art. In general, the tensile strength of the fibrin microthreads can range from more than about 0.1 MPa (e.g., 0.2, 0.4, 0.5, 1.0, 2.0, 4.0) to less than about 25 MPa (e.g., 22 MPa, 20 MPa, 18 MPa, 15 MPa, 10 MPa).

The biological activity of the fibrin microthreads, e.g., the capacity of to mediate tissue regeneration, can be assayed by any method known to those of skill in the art. Examples include measuring cell ingrowth, cell proliferation, cell orientation and alignment relative to the fibrin microthread axis.

A therapeutic agent, for example, a growth factor, a protein, a chemotherapeutic agent, a vitamin, a mineral, an antimicrobial agent, a small organic molecule, or a biological cell can be added by and (a) extruding the therapeutic agent with the fibrinogen and the molecule thereby producing a fibrin microthread comprising the therapeutic agent or (b) associating the therapeutic agent with a formed fibrin microthread. The therapeutic agent can be covalently bonded to the fibrin microthread. The bonding agent can be a ligase, wherein the ligase generates a carbon-oxygen bond, a carbon-sulfur bond, a carbon-nitrogen bond, or a carbon-carbon bond between the therapeutic agent and the fibrin microthread.

The fibrin microthreads can be configured in many farms according to the size and shape of the tissue repair that is desired. The coextrusion step may be repeated one or more times to produce a multifilament fibrin microthread scaffold. Alternatively the Fibrin microthreads can be assembled into hierarchically organized structures such as woven fabrics or ropes of variable size, shape, and character, which may be used alone or in conjunction with other tissue repair materials such as woven or non-woven meshes, pins, screws, plates, patches, filaments, and natural or mechanical valves. The microthreads may be present, for example, as a reinforcing element. The mechanical properties, surface chemistries and porosities of the microthreads can be varied and controlled to direct, alter, and/or facilitate multidimensional cellular alignment and tissue regeneration.

The compositions, whether used alone or in combination with another repair substance or device can be shaped in the form of a mesh, dressing, gauze, web, film, patch, sheath or graft for application to or implantation in tissue in need of repair. For example fibrin microthread compositions may be woven or braided or otherwise attached to other polymers or tissue repair compositions. The fibrin microthread can be combined with a microthread comprising a non-fibrin polymer. Synthetic polymers include the synthetic polymer comprises an aliphatic polyester, a poly(amino acid), poly(propylene fumarate), a copoly(ether-ester), a polyalkylene oxalate, a polyamide, a tyrosine-derived polycarbonate, a poly(iminocarbonate), a polyorthoester, a polyoxaester, a polyamidoester, a polyoxaester containing one or more amine groups, a poly(anhydride), a polyphosphazine, a polyurethane, a biosynthetic polymer, or a combination thereof. The aliphatic polyester comprises homopolymers or copolymers of: lactides; glycolides; ε-caprolactone; hydroxybuterate; hydroxyvalerate; 1,4-dioxepan-2-one; 1,5,8,12-tetraoxyacyclotetradecane-7,14-dione; 1,5-dioxepan-2-one; 6,6-dimethyl-1,4-dioxan-2-one; 2,5-diketomorpholine; p-dioxanone(1,4-dioxan-2-one); trimethylene carbonate(1,3-dioxan-2-one); alkyl derivatives of trimethylene carbonate; δ-valerolactone; β-butyrolactone; γ-butyrolactone, ε-decalactone, pivalolactone, α,α-diethylpropiolactone, ethylene carbonate, ethylene oxalate; 3-methyl-1,4-dioxane-2,5-dione; 3,3-diethyl-1,4-dioxan-2,5-dione; 6,8-dioxabicyclooctane-7-one; or combinations thereof. Other polymers can include polymers derived from natural sources e.g., collagen and collagen based-compositions. A biosynthetic polymer can include a polymer comprising a sequence found in collagen, elastin, thrombin, fibronectin, a starch, gelatin, alginate, pectin, oxidized cellulose, chitin, chitosan, tropoelastin, hyaluronic acid, a ribonucleic acid, a deoxyridonucleic acid, a polypeptide, a polysaccharide, or a combination thereof. Or a natural polymer for example collagen or a collagen-based material, hyaluronic acid or a hyaluronic acid-based material, cellulose or a cellulose-based material, silk and combinations thereof.

Alternatively or in addition, such composition may be synthetic in origin. Examples of commercially available polypropylene meshes can include: Marlex™ (CR Bard, Inc., Cranston, R.I.), Visilex® (CR Bard, Inc., Cranston, R.I.), PerFix® Plug (CR Bard, Inc., Cranston, R.I.), Kugel™ Hernia Patch (CR Bard, Inc., Cranston, R.I.), 3DMax® (CR Bard, Inc., Cranston, R.I.), Prolene™ (Ethicon, Inc., Somerville, N.J.), Surgipro™ (Autosuture, U.S. Surgical, Norwalk, Conn.), Prolite™ (Atrium Medical Co., Hudson, N.H.), Prolite Ultra™ (Atrium Medical Co., Hudson, N.H.), Trelex™ (Meadox Medical, Oakland, N.J.), and Parietene® (Sofradim, Trévoux, France). Examples of commercially available polyester meshes include Mersilene™ (Ethicon, Inc., Somerville, N.J.) and Parietex® (Sofradim, Trévoux, France). Examples of commercially available PTFE meshes include Goretex® (W.L. Gore & Associates, Newark, Del.), Dualmesh® (W.L. Gore & Associates, Newark, Del.), Dualmesh® Plus (W.L. Gore & Associates, Newark, Del.), Dulex® (CR Bard, Inc., Cranston, R.I.), and Reconix® (CR Bard, Inc., Cranston, R.I.).

Other useful compositions include resorbable meshes. Polymers used to make resorbable meshes can include polyglycolic acid (Dexon™, Syneture™, U.S. Surgical, Norwalk, Conn.), poly-1-lactic acid, polyglactin 910 (Vicryl™, Ethicon, Somerville, N.J.), or polyhydroxylakaoate derivatives such as poly-4-hydroxybutyrate (Tepha, Cambridge, Mass.). Composite meshes, i.e., meshes that include both resorbable and non-resorbable materials can be made either from combinations of the materials described above or from additional materials. Examples of commercially available composite meshes include polypropylene/PTFE: Composix® (CR Bard, Inc., Cranston, R.I.), Composix® E/X (CR Bard, Inc., Cranston, R.I.), and Ventralex® (CR Bard, Inc., Cranston, R.I.); polypropylene/cellulose: Proceed™ (Ethicon, Inc., Somerville, N.J.); polypropylene/Seprafilm®: Sepramesh® (Genzyme, Cambridge, Mass.), Sepramesh® IP (Genzyme, Cambridge, Mass.); polypropylene/Vicryl: Vypro™ (Ethicon, Somerville, N.J.), Vypro™ II (Ethicon, Somerville, N.J.); polypropylene/Monocryl(poliglecaprone): Ultrapro® (Ethicon, Somerville, N.J.); and polyester/collagen: Parietex® Composite (Sofradim, Trévoux, France).

The step of combining the fibrin microthread with a microthread comprising a non-fibrin polymer can include weaving the fibrin microthread and the microthread comprising the non-fibrin polymer, bundling the fibrin microthread and the microthread comprising the non-fibrin polymer to form a filament, or tying or interlacing the fibrin microthread and the microthread comprising the non-fibrin polymer to form a non-woven mesh, associating the fibrin microthread with a substrate or a woven or non-woven mesh, a surgical pin, a surgical screw, a surgical plate, a physiologically acceptable patch, dressing, bandage, or a natural or mechanical valve. The fibrin microthread compositions may be used in the preparation of a medicament for tissue repair, wherein the tissue repair comprises tissue augmentation or the replacement of all or part of a tissue. The tissue repaired comprises skin, muscle, or a connective tissue.

III. Tissue and Organ Repair

The biocompatible tissue repair compositions described herein can be used to treat any of a wide range of disorders in which amelioration or repair of tissue is needed. Tissue defects can arise from diverse medical conditions, including, for example, congenital malformations, traumatic injuries, infections, and oncologic resections. Thus, the biocompatible tissue repair compositions can be used to repair defects in any soft tissue, e.g., tissues that connect support or surround other structures and organs of the body. Soft tissue can be any non-osseous tissue. Soft tissue can be epithelial tissue, which covers the outside of the body and lines the organs and cavities within the body. Examples of epithelial tissue include, but are not limited to, simple squamous epithelia, stratified squamous epithelia, cuboidal epithelia, or columnar epithelia.

Soft tissue can also be connective tissue, which functions to bind and support other tissues. One example of connective tissue is loose connective tissue (also known as areolar connective tissue). Loose connective tissue, which functions to bind epithelia to underlying tissues and to hold organs in place, is the most widely distributed connective tissue type in vertebrates. It can be found in the skin beneath the dermis layer; in places that connect epithelium to other tissues; underneath the epithelial tissue of all the body systems that have external openings; within the mucus membranes of the digestive, respiratory, reproductive, and urinary systems; and surrounding the blood vessels and nerves. Loose connective tissue is named for the loose "weave" of its constituent fibers which include collagenous fibers, elastic fibers (long, threadlike stretchable fibers composed of the protein elastin) and reticular fibers (branched fibers consisting of one or more types of very thin collagen fibers): Connective tissue can also be fibrous connective tissue, such as tendons, which attach muscles to bone, and ligaments, which joint bones together at the joints. Fibrous connective tissue is composed primarily of tightly packed collagenous fibers, an arrangement that maximizes tensile strength. Soft tissue can also be muscle tissue; muscle tissue includes skeletal muscle, which is responsible for voluntary movements; smooth muscle, which is found in the walls of the digestive tract, bladder arteries and other internal organs; and cardiac muscle, which forms the contractile wall of the heart.

The biocompatible tissue repair compositions can be used to repair soft tissues in many different organ systems that fulfill a range of physiological functions in the body. These organ systems can include, but are not limited to, the muscular system, the genitourinary system, the gastroenterological system, the integumentary system, the o circulatory system and the respiratory system. The compositions are particularly useful for repairs to connective tissue, for example, tendons and ligaments.

The biocompatible tissue repair compositions are suitable for hernia repair. A hernia is the protrusion of the contents of a body cavity out of the body cavity in which the contents are normally found. These contents are often enclosed in the thin membrane that lines the inside of the body cavity; together the membrane and contents are referred to as a "hernial sac". Most commonly hernias develop in the abdomen, when a weakness in the abdominal wall expands into a localized hole or defect through which the protrusion occurs. These weaknesses in the abdominal wall typically occur in locations of natural thinning of the abdominal wall, that is, at sites where there are natural openings to allow the passage of canals for the blood vessels that extend from the abdomen to the extremities and other organs. Other areas of potential weakness are sites of any previous abdominal surgery. Fatty tissue usually enters a hernia first, but it can be followed by a segment of intestine or other intraabdominal organ. Ma segment of internal organ becomes trapped within the hernial sac such that the blood supply to the organ is impaired, the patient is at risk for serious complications including intestinal blockage, gangrene, and death. Hernias do not heal spontaneously and often increase in size over time, so that surgical repair is necessary to correct the condition. In general, hernias are repaired by reinserting the hernial sac back into the body cavity followed by repair of the weakened muscle tissue.

In contrast to hernias of congenital origin, incisional hernias, also known as ventral or recurrent hernias, occur in the abdomen in the area of an old surgical scar. Incisional hernias have a higher risk of returning after surgical repair than do congenital hernias. Moreover, in the case of multiple recurrent hernias, i.e., hernias that recur after two or more repairs have been carried out, the likelihood of successful repair decreases with each subsequent procedure.

The compositions can be used to treat other medical conditions that result from tissue weakness. One condition for which the biocompatible tissue repair compositions are useful is in the repair of organ prolapse. Prolapse is a condition in which an organ, or part of an organ, falls or slips out of place. Prolapse typically results from tissue weakness that can stem from either congenital factors, trauma or disease. Pelvic organ prolapse can include prolapse of one or more organs within the pelvic girdle; tissue weakening due to pregnancy, labor and childbirth is a common cause of the condition in women. Remedies include both non-surgical and surgical options; in severe cases, reconstruction of the tissues of the pelvic floor, i.e., the muscle fibers and connective tissue that span the area underneath the pelvis and provides support for the pelvic organs, e.g., the bladder, lower intestines, and the uterus (in women) may be required.

The biocompatible tissue repair compositions are also useful in repairs of the gastrointestinal system. Esophageal conditions in need of repair include, but are not limited to, traumatic rupture of the esophagus, e.g., Boerhaave syndrome, Mallory-Weiss syndrome, trauma associated with iatrogenic esophageal perforation that may occur as a complication of an endoscopic procedure or insertion of a feeding tube or immolated surgery; repair of congenital esophageal defects, e.g., esophageal atresia; and oncologic esophageal resection.

The compositions can be used to repair tissues that have never been repaired before or they can be used to repair tissues that have been treated one or more times with compositions or with other methods known in the art or they can be used along with other methods of tissue repair including suturing, tissue grafting, or synthetic tissue repair materials.

The compositions can applied to an individual in need of treatment using techniques known to those of skill in the art. The biocompatible tissue repair compositions can be: (a) wrapped around a tissue that is damaged or that contains a defect; (b) placed on the surface of a tissue that is damaged or has a defect; (c) rolled up and inserted into a cavity, gap, or space in the tissue. One or more (e.g., one, two, three, four, five, six, seven, eight, nine, ten, 12, 14, 16, 18, 20, 25, 30, or more) such compositions, stacked or adjacent to each other, can be used at any particular site. The compositions can be held in place by, for example, sutures, staples, tacks, or tissue glues or sealants known in the art. Alternatively, if, for example, packed sufficiently tightly into a defect or cavity, they may need no securing device.

In accordance with the present teachings, the invention features methods of making a fibrin microthread composition. The methods can include or can consist of the steps: (a) providing fibrinogen and a sufficient amount of a molecule capable of forming fibrin from the fibrinogen; and (b) extruding a mixture of the fibrinogen and the molecule through an orifice into a medium thereby producing a fibrin microthread. The fibrinogen can be human fibrinogen or fibrinogen of a non-human primate, a domesticated animal (e.g., a cat, dog, or horse), or a rodent (e.g., a rat or mouse). Regardless of the precise source, sequence, state of glycosylation, or other characteristic, the fibrinogen can be obtained from (e.g., isolated or purified from) a naturally occurring source (e.g., the fibrinogen can be 70%, 80%, 90%, 95% or more pure) can be recombinantly produced. Fragments or variants of fibrinogen as well as fibrinogen-like proteins (e.g., FReP-A, FReP-B, the C terminus of the *Drosophila* protein scabrous or the C terminus of a mammalian Tenascin or prothrombinase) can also be used so long as they can provide polymerizable fibrin. The molecule can be a protease (e.g., thrombin or a biologically active variant thereof).

The medium can be a buffered solution (e.g., a solution having a pH of about 4.0-8.0 (e.g., 6.0 to about 8.0 or 6.5 to 7.5 or 7.0 to 7.5 (e.g., about 7.4). The medium can be contained within a container having a non-stick surface (e.g., Teflon®) for receiving the fibrin microthread. Alternatively, or in addition, the medium can be physically agitated (e.g., stirred) to help prevent the microthreads from sticking to the receiving container.

In any of the methods, the fibrin microthreads can be recovered from the medium and permitted to dry.

In any of the methods, the extruding step can be carried out at a temperature between about 25° C. and about 42° C., inclusive (e.g., at about 25, 26, 27, 28, 29, 30, 35, 40, or 42° C.) and the orifice can have a variable diameter (e.g., a diameter of about 0.2 μm to about 1,000 μm (e.g., about 20 μm to about 100 μm; about 30 μm; about 50 μm; about 150 μm about 200 μm; about 250 μm; about 300 μm; or about 380 μm).

In any of the methods, one can also provide a therapeutic agent and (a) extrude the therapeutic agent with the fibrinogen and the molecule thereby producing a fibrin microthread comprising the therapeutic agent or (b) associate the therapeutic agent with a formed fibrin microthread. The therapeutic agent can be a growth factor, a protein, a chemotherapeutic agent, a vitamin, a mineral, an antimicrobial agent (e.g., an antibacterial agent, an antiviral agent, an antifungal agent, or an antiparasitic agent), a small organic molecule, or a biological cell. Associating the therapeutic agent with a formed fibrin microthread can be achieved by covalently bonding the therapeutic agent to the fibrin microthread (by, for example, exposing the therapeutic agent and the fibrin microthread to a ligase that, for example, generates a carbon-oxygen bond, a carbon-sulfur bond, a carbon-nitrogen bond, or a carbon-carbon bond between the therapeutic agent and the fibrin microthread). One can also expose the therapeutic agent and the fibrin microthread to a crosslinking agent (e.g., a chemical crosslinking agent or ultraviolet radiation).

The growth factor can be a cytokine or interleukin. The growth factor can be an epidermal growth factor, a fibroblast growth factor (e.g., basicFGF), a glial growth factor, a granulocyte-macrophage colony-stimulating factor, an insulin-like growth factor (e.g., IGF-1 or IGF-2), a nerve growth factor, a platelet-derived growth factor, stem cell growth factor, or a transforming growth factor (e.g., TGFβ). The interleukin can be IL-2 or IL-17. The protein can be a hormone, an extracellular matrix protein (e.g., collagen, elastin, laminin, tenascin, or fibronectin), or an antibody.

In any of the methods, one can also combine a fibrin microthread with a microthread comprising a non-fibrin polymer (e.g., a synthetic or natural polymer other than fibrin). The synthetic polymer can be or can include an aliphatic polyester, a poly(amino acid), poly(propylene fumarate), a copoly(ether-ester), a polyalkylene oxalate, a polyamide, a tyrosine-derived polycarbonate, a poly(iminocarbonate), a polyorthoester, a polyoxaester, a polyamidoester, a polyoxaester containing one or more amine groups, a poly(anhydride), a polyphosphazine, a polyurethane, a biosynthetic polymer, or a combination thereof. The method aliphatic polyester can be or can include homopolymers or copolymers of lactides; glycolides; ε-caprolactone; hydroxybuterate; hydroxyvalerate; 1,4-dioxepan-2-one; 1,5,8,12-tetraoxyacyclotetradecane-7,14-dione; 1,5-dioxepan-2-one; 6,6-dimethyl-1,4-dioxan-2-one; 2,5-diketomorpholine; p-dioxanone (1,4-dioxan-2-one); trimethylene carbonate(1,3-dioxan-2-one); alkyl derivatives of trimethylene carbonate; δ-valerolactone; β-butyrolactone; γ-butyrolactone, ε-decalactone, pivalolactone, α,α-diethylpropiolactone, ethylene carbonate, ethylene oxalate; 3-methyl-1,4-dioxane-2,5-dione; 3,3-diethyl-1,4-dioxan-2,5-dione; 6,8-dioxabicycloctane-7-one; or combinations thereof. The biosynthetic polymer can be or can include a polymer comprising a sequence found in collagen, elastin, thrombin, fibronectin, a starch, gelatin, alginate, pectin, oxidized cellulose, chitin, chitosan, tropoelastin, hyaluronic acid, a ribonucleic acid, a deoxyribonucleic acid, a polypeptide, a polysaccharide, or a combination thereof. The natural polymer can be or can include collagen or a collagen-based material, hyaluronic acid or a hyaluronic acid-based material, cellulose or a cellulose-based material, silk and combinations thereof.

In any of the methods utilizing more than one, microthread, the step of combining a fibrin microthread with a microthread comprising a non-fibrin polymer can include weaving the fibrin microthread and the microthread comprising the non-fibrin polymer, bundling the fibrin microthread and the microthread comprising the non-fibrin polymer to form a filament, or tying or interlacing the fibrin microthread and the microthread comprising the non-fibrin polymer to form a non-woven mesh. The fibrin microthread and the microthread comprising the non-fibrin polymer can be coextruded. For example, a fibrin microthread can be extruded through one orifice into a receptacle and a non-fibrin microthread can be extruded through a second orifice into the same or a separate receptacle.

Any of the fibrin microthreads or the fibrin microthread compositions can be associated with a substrate (by, for example, coating, wrapping, or otherwise permanently or non-permanently associating the microthreads or microthread compositions with the substrate). The substrate can be a woven or non-woven mesh, a surgical pin, a surgical screw, a surgical plate, or the like, a physiologically acceptable patch (as is used, for example, in hernia repair), a dressing, bandage, or a natural or mechanical valve.

The invention encompasses a fibrin microthread composition made by any of the methods described herein and any tissue engineering construct (e.g., a hydrogel) that includes the fibrin microthreads or fibrin microthread compositions described herein.

The invention encompasses use of fibrin microthread composition made by any of the methods described herein and any tissue engineering construct (e.g., a hydrogel) that includes the fibrin microthreads or fibrin microthread compositions described herein in the preparation of a medicament and/or in the preparation of a medicament for tissue repair. The tissue repair comprises tissue augmentation or the replacement of all or part of a tissue, and the tissue repaired can be or can include skin, muscle, or a connective tissue. The tissue repair can be necessitated by a traumatic injury, a congenital malformation, or tissue loss, malfunction, or malformation resulting from an infection or surgical procedure.

The invention features methods of treatment comprising: (a) identifying a mammalian subject as having a recipient organ or tissue in need of repair; and (b) placing the fibrin microthread composition as described herein or the tissue engineering construct described herein in or on the organ or tissue. The subject can be a human.

The invention features an article of manufacture comprising a measured amount of fibrin microthreads and one or more items selected from the group consisting of packaging material, a package insert comprising instructions for use, and a sterile container.

EXAMPLES

Example 1

Materials and Methods

Fibrin microthread preparation: Fibrin microthreads were co-extruded from solutions of fibrinogen and thrombin according to the schematic shown in FIG. 1. Fibrinogen from bovine plasma (Sigma, St. Louis, Mo., catalogue number F4753) was dissolved in HEPES Buffered Saline (HBS, 20 mM HEPES, 0.9% NaCl) at 70 mg/mL and stored at −20° C. Thrombin from bovine plasma (Sigma, St. Louis, Mo., catalogue number T4648) was stored frozen as a stock solution at a concentration of 40 U/mL in HBS. A working solution of thrombin was diluted from the stock to a final concentration of 6 U/mL in a 40 mM $CaCl_2$ solution. Both the fibrinogen and thrombin solutions were warmed to 37° C. and placed into separate 1 mL syringes. The solutions were coextruded using a stabilized crosshead on a threaded rod with a crosshead speed of 4.25 mm/min through a blending applicator tip (Micromedics, Inc., St. Paul, Minn.). The blending applicators were Luer locked to the two syringes through individual bores and mixed in a needle that was Luer locked to the tip. The solutions were combined and extruded through polyethylene tubing (BD, Sparks, Md.) with an inner diameter of 0.38 mm into a bath of 10 mM HEPES, pH 7.4 at room temperature. The threads were hand-drawn through the bath at a rate approximately matching the flow rate of the polymerization solution form the tubing. The bath was contained in a vessel that had a Teflon®-coated surface. Finally, threads were removed from the bath, air dried under the tension of their own weight, and stored at room temperature in a desiccator until use.

Fibrin microthread crosslinking. Microthreads were crosslinked by UV irradiation. Microthreads were placed on a reflective aluminum foil surface that was centered 11 cm from a bank of 5-8 watt UV tubes emitting at a primary wavelength of 254 nm in a model CL-WOO ultraviolet crosslinker (UVP, Upland, Calif.). The microthreads were exposed for 0, 20, 40, 60, and 120 minutes and therefore received a calculated total energy of 8.5, 17.1, 25.7, 51.3 $J/cm^2$. Controls were left uncrosslinked (0 $J/cm^2$).

Scanning Electron Microscopy (SEM). Fibrin microthreads were imaged with a scanning electron microscope to characterize thread morphology and surface topography. Air dried fibrin threads were mounted on aluminum stubs (Ted Pella, Inc., Redding, Calif.) coated with double-sided carbon tape and sputtered coated with a thin layer of gold-palladium for 2 minutes. Images were acquired at 15 kV using a JSM-KLG scanning electron microscope.

Thread Swelling. Qualitative volumetric analyses were based on the swelling ratios of fibrin microthreads. The cross-sectional area of each thread was calculated from an average of three diameter measurements along its length, assuming cylindrical thread geometry. The diameters were measured both dry and after hydration for at least 30 minutes in phosphate buffered saline (PBS) using a 20× objective on a Nikon Eclipse E400 microscope fitted with a calibrated reticule. The swelling ratio was calculated as the ratio of the wet cross-sectional area to the dry cross-sectional area for each discrete thread.

Mechanical Properties. Fibrin microthreads were hydrated and mechanically loaded in uniaxial tension to obtain stress-strain curves. Individual threads were mounted vertically with adhesive (Silastic Silicone Type A, Dow Corning) on vellum frames with precut windows that defined the region of loading. For tensile testing, the samples in the vellum frames were clamped into a custom designed micromechanical testing unit consisting of a horizontal linearly actuated crosshead and a fixed 150 g load cell. An initial gauge length of 20 mm was defined as the distance between adhesive spots across the precut window in the vellum frame. Test unit operations and data acquisition were controlled with LabView software (National Instruments, Austin, Tex.). Threads were hydrated for at least 30 minutes prior to testing, but were not tested submerged. After loading into the testing apparatus, the edges of each frame were cut leaving the thread intact. The threads were then loaded to failure at a 50% strain rate (10 mm/min). Curves of the $1^{st}$ Piola Kirchhoff stress versus Green's strain were calculated from the load displacement data assuming a cylindrical cross-sectional area of each thread and calculating cross-sectional area based on thread diameter measurements as described above for swelling ratio. Post-processing of the mechanical data considered a strain of zero to be when a thread was minimally loaded to a nominal threshold of 0.01 grams, or less than 1% of the ultimate load for the weakest uncrosslinked thread. Ultimate tensile strengths (UTS), strains at failure (SAF), and the maximum tangent moduli or stiffnesses (E) were calculated from the stress-strain curves. The stiffness was defined as the maximum value for a tangent to the stress-strain curve over an incremental strain of 0.03.

Cell Proliferation. Normal human dermal fibroblasts were isolated from neonatal foreskins. Foreskins were trimmed with scissors to remove excess fatty tissue, rinsed repeatedly with sterile phosphate-buffered saline, and diced into small fragments. The fragments were allowed to adhere to the bottom of a tissue culture plate in a humidified 10% CO2 atmosphere at 37° C. for 1 hour, and were then covered with Dulbecco's modified Eagle's medium (DMEM; high glucose, Gibco BRL, Gaithersburg, Md.) supplemented with 20% fetal bovine serum (FBS; JRH Biosciences, Lenexa, KS) containing 100 U of penicillin and 100 μg of streptomycin (Gibco BRL) per ml. Over a period of 14 days, fibroblasts migrated from the tissue fragments and formed a confluent layer on the tissue culture plate. Fibroblasts were cultured in Dulbecco's Modified Eagle's Medium (DMEM; Gibco BRL, Gaithersburg, Md.) supplemented with 10% fetal bovine serum (FBS; Atlanta Biologicals, Lawrenceville, Ga.) and penicillin/streptomycin (100 U/100 mg per mL; Gibco BRL) in an incubated chamber maintained at 37° C. and 10% $CO_2$. Passages 4-7 were used during experiments.

To characterize cell attachment and proliferation, bundles of 10 fibrin threads 1.5 cm long, (uncrosslinked fibrin, UV crosslinked fibrin (40 minutes), or polypropylene controls (Prolene 7-0 suture)) were glued to Thermanox™ coverslips (Nalge Nunc International, Rochester, N.Y.) with silicone adhesive (Silastic Silicone Type A, Dow Corning) and placed individually inside standard 35 mm culture dishes. Thread bundles were rehydrated in PBS for 15 minutes, sterilized with 70% isopropyl alcohol for 1 hour and rinsed in sterile PBS for 15 minutes, 3 times. Following standard procedure for passaging, fibroblasts were released from monolayer culture with trypsin, centrifuged, and resuspended at a concentration of 500,000 cells/mL. Each sterilized thread bundle was seeded with 100 μL of cells in media with 10% FBS and incubated for 30 minutes. Two mL of media were then added to each culture dish and returned to incubation conditions. Fibroblast attachment and proliferation was visualized at days 1 and 7 with a Live/Dead cell viability stain (Molecular Probes, Eugene, Oreg.). At each time point, after removal of media, 1.5 mL of a 4 μM ethidium homodimer-1 and 2 μM calcein AM solution were added to each bundle of threads and incubated at room temperature. Calcein (green, Ex/em 495 nm/515 nm) is retained in living cells while ethidium (red, Ex/em 495 nm/635 nm) is excluded by intact plasma membranes, but enters damaged membranes where it can fluoresce upon binding to nucleic acid. Thread bundles were cut from Thermanox™ coverslips and placed on slides for fluorescent imaging. Images were acquired on a Nikon Eclipse E400 microscope using a Texas Red filter cube.

Statistical Analyses. Statistical differences between means of the data were conducted by one-way ANOVA with pairwise multiple comparisons (Holm-Sidak method) using SigmaStat (Systat Software Inc., Point Richmond, Calif.). Values reported are means and standard deviations unless otherwise stated. A $p<0.009$ indicated a significant difference between experimental groups.

Example 2

Analysis of Coextrusion Parameters

The effect of coextrusion rate, and pH and temperature of the aqueous bath on fibrin microthread tensile properties was analyzed. Coextrusion rate was expressed as a "rate ratio", i.e., the ratio of flow velocity/plotter velocity, where flow velocity is the speed with which the fibrin solution emerges from the tubing and plotter velocity is the speed of the extrusion tubing through the aqueous bath. For example, a rate ratio of 2.0 describes extrusion parameters in which the solution flows out of the tubing twice as fast as the tubing tip moves through the aqueous bath. Fibrinogen and thrombin solutions were prepared according to the method in Example 1 and coextruded with rate ratios of either 1.0, 2.0, or 4.0, and analyzed for tensile strength according to the method in Example 1. Increasing the rate ratio from 1.0 to 2.0 resulted in a three-fold increase in ultimate tensile strength and about a ten-fold increase in load to failure. A further increase from 2.0 to 4.0 resulted in a decrease in ultimate tensile strength, but had minimal effect on load to failure. The ultimate tensile strength averaged 4.78 MPa for a rate ratio of 2.0, while ratios above and below generated in fibrin microthreads with statistically significantly lower tensile strength. The load to failure for rate ratios of 2.0 and 4.0 were roughly similar and both were greater than that obtained for the rate ratio of 1.0. Increasing the rate ratio increased both the wet diameter and the strain to failure in a roughly linear fashion.

The effect of pH of the aqueous bath on fibrin microthread tensile strength was also analyzed. Fibrinogen and thrombin solutions were prepared according to the method in Example 1 and coextruded into solutions of 10 mM HEPES-buffered saline at either pH 6.0, 7.42, or 8.5. At physiological pH (7.42) and higher (8.5) the ultimate tensile strength of the resulting fibrin microthread was about seven- and five-fold greater, respectively than that of fibrin microthreads formed at pH 6.0.

The effect of the temperature of the aqueous bath on fibrin microthread tensile strength was also analyzed. Fibrinogen and thrombin solutions were prepared according to the method in Example 1 and coextruded into a solution of 10 mM HEPES-buffered 7.42 at either 20° C. or 37° C. The ultimate tensile strength of the fibrin microthreads formed at 20° C. was statistically significantly greater than those produced at 37° C.

Example 3

Fibrin Microthread Structure and Morphology

Figure 2:
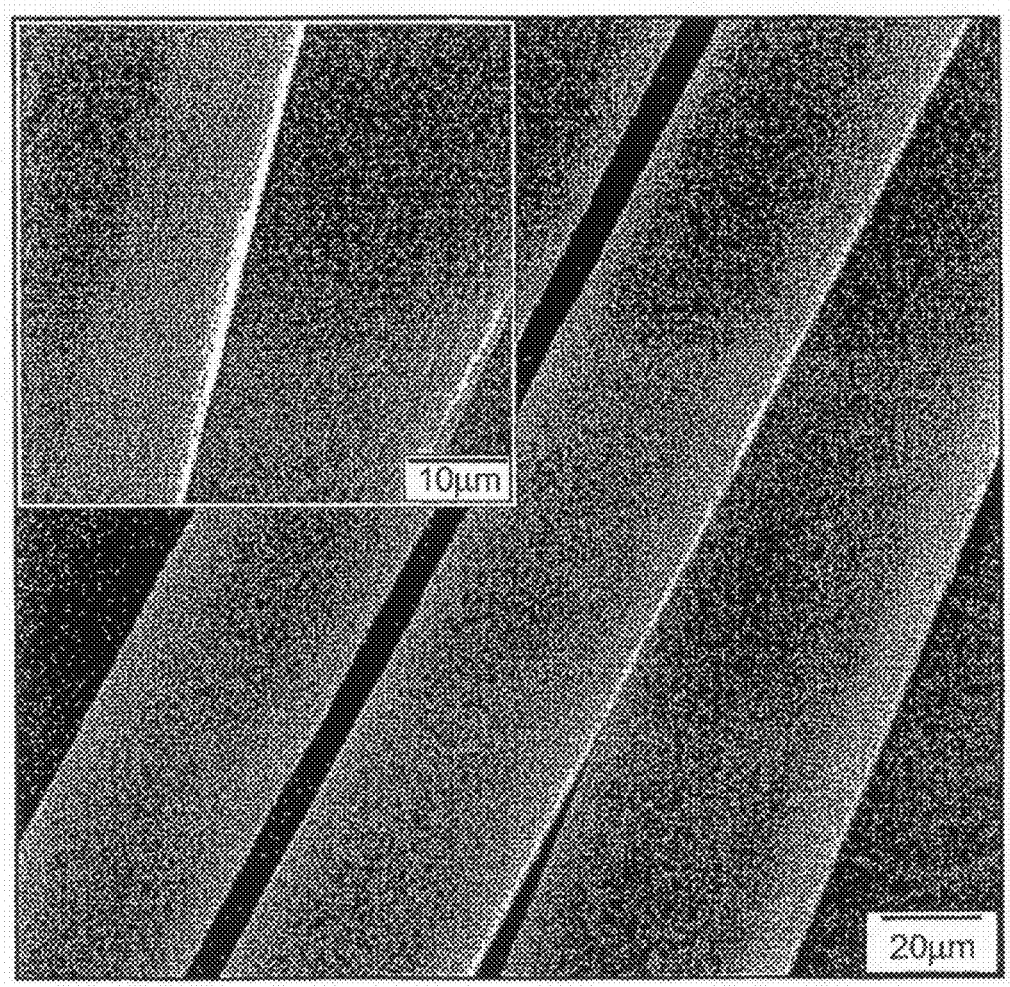
FIG. 2 depicts a scanning electron micrograph of fibrin microthreads.
Figure 3:
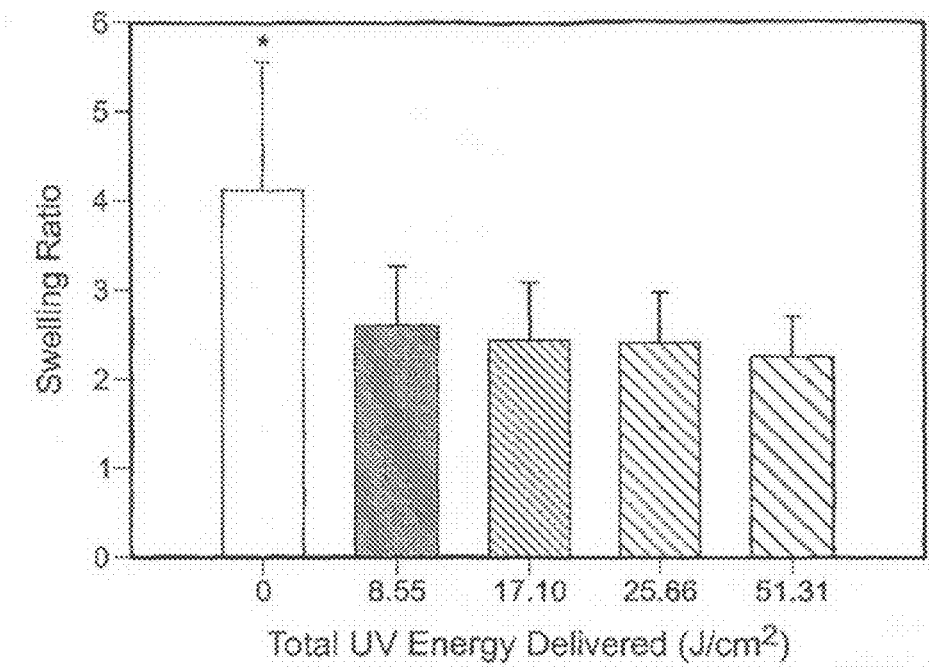
FIG. 3 depicts the results of an experiment analyzing the effect of UV cross-linking on fibrin microthread swelling ratio.

The structure and morphology of fibrin microthreads were analyzed with light and scanning electron microscopy techniques. The transparent solutions of fibrinogen and thrombin were co-extruded into the bath. Within 5 minutes threads formed, largely at the bottom of the bath. Upon removal from the buffer and air drying, the threads elongated considerably under their own weight, stretching in length while decreasing in initial cross-sectional area. After drying, all fibrin threads visually appeared to have relatively consistent gross structure and morphology that remained unchanged after crosslinking. The dry diameters of the microthreads ranged from 20 to 50 μm with an average of 34.6 μm and a median of 35 μm. SEM analyses indicated that the fibrin threads had relatively smooth surfaces with regular, submicron surface topographies (FIG. 2). Upon rehydration in PBS, uncrosslinked fibrin threads swelled to more than 4 times their dry cross-sectional areas (Table I). In contrast, threads that were crosslinked with UV light swelled significantly less than uncrosslinked threads, achieving swelling ratios that peaked at approximately 2.5 and decreased slightly with increased exposure times. The effect of UV cross-linking on fibrin microthread swelling ratio is shown in FIG. 3.

TABLE 1

The cross-sectional area and swelling ratio of fibrin microthreads with increased UV cross-linking

| UV Exposure time (min) | Power (J/cm2) | Sample Size (n) | Dry Area (uM) | Hydrated Area (uM) | Swelling Ratio |
|---|---|---|---|---|---|
| 0 | 0.00 | 13 | 910 ± 400 | 3200 ± 1670 | 4.09 ± 1.48 |
| 20 | 8.55 | 19 | 1210 ± 560 | 2950 ± 1550 | 2.59 ± 0.66 |
| 40 | 17.10 | 18 | 1070 ± 410 | 2490 ± 1020 | 2.42 ± 0.65 |
| 60 | 25.66 | 18 | 1210 ± 570 | 2820 ± 1440 | 2.38 ± 0.57 |
| 120 | 51.31 | 12 | 940 ± 250 | 1890 ± 820 | 2.24 ± 0.44 |

Example 4

Fibrin Microthread Mechanical Properties

Figure 4:
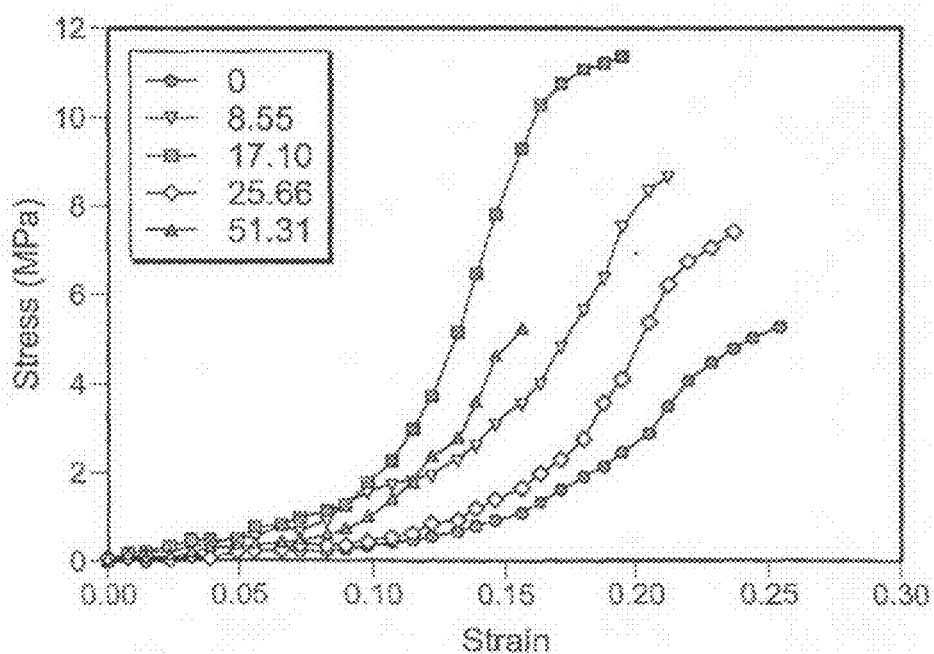
FIG. 4 depicts characteristic stress-strain curves for fibrin microthreads.
Figure 5:
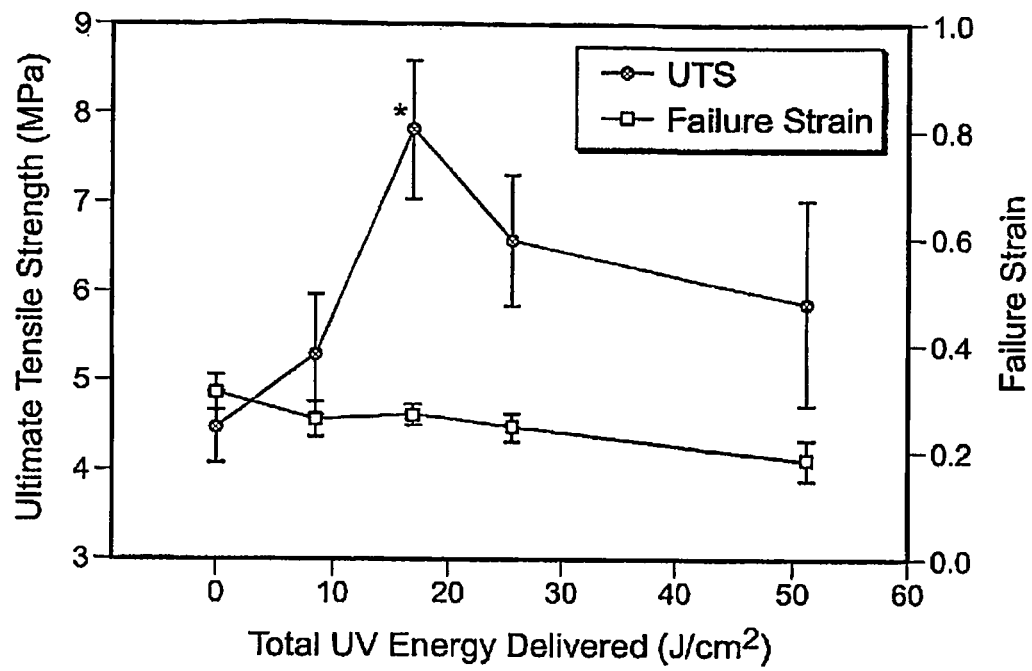
FIG. 5 depicts the results of an experiment analyzing the effect of UV cross-linking on UTS and failure strain for fibrin microthreads.
Figure 6:
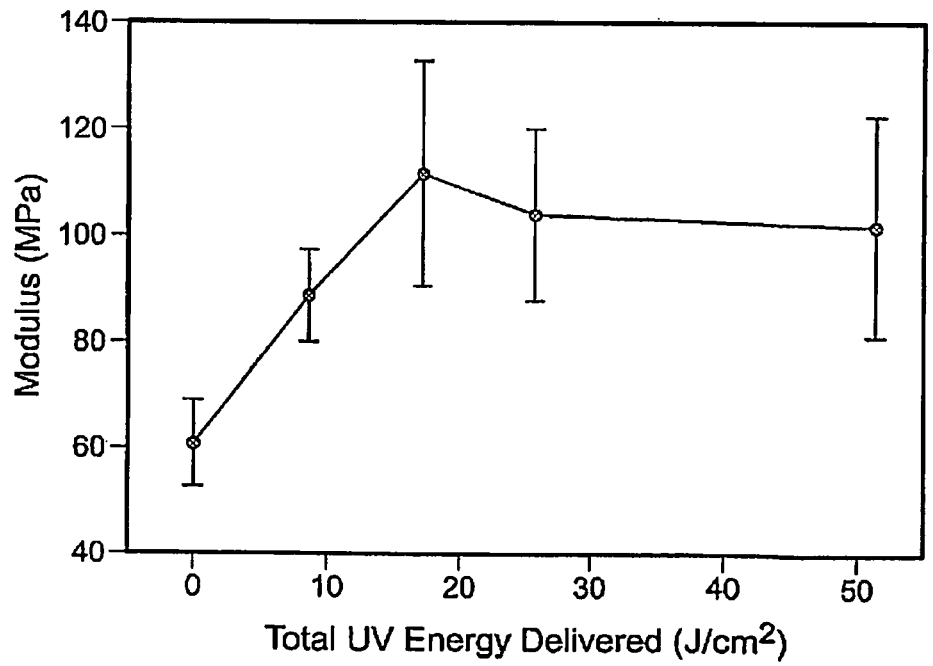
FIG. 6 depicts the results of an experiment analyzing the effect of UV cross-linking on stiffness of fibrin microthreads.

The mean ultimate tensile strengths (UTS), failure strains, and moduli of mechanically tested discrete fibrin microthreads are summarized in Table 2. In general, fibrin threads exhibited extended initial toe regions of increasing elongation with little increase in stress follow by a rapid ascension in stress until failure. Characteristic stress-strain curves for fibrin microthreads are shown in FIG. 4. Uncrosslinked threads attained average UTS of 4.48 MPa, typically breaking at strains of less than one-third of the original lengths of the threads. The UTS of the threads increased with UV exposure. The maximal strengths were achieved when threads were exposed to 17.10 J/cm$^2$ of UV light. The strengths measured at this exposure level were significantly greater than other conditions tested in this study. The effect of UV cross-linking on UTS and failure strain are shown in FIG. 5. While the strains to failure exhibited a small declining trend with increased UV exposure, the decrease was nominal and not significantly different (FIG. 5). The modulus, measured as the maximum tangent modulus over an incremental strain of 0.03, established a similar trend to UTS. This measure of the bulk material stiffness increased with UV exposure before reaching a plateau when threads were treated with 17.10 J/cm$^2$ of UV energy. The effect of UV cross-linking on stiffness of fibrin microthreads is shown in FIG. 6.

TABLE 2

The mechanical properties of fibrin microthreads with increased UV cross-linking

| UV Exposure time (min) | Power (J/cm2) | Sample Size (n) | Strength UTS (MPa) | Failure Strain, SAF | Modulus, E (MPa) |
|---|---|---|---|---|---|
| 0 | 0.00 | 22 | 4.48 ± 1.79 | 0.31 ± 0.15 | 60.70 ± 25.71 |
| 20 | 8.55 | 19 | 5.29 ± 2.78 | 0.26 ± 0.13 | 88.54 ± 27.53 |
| 40 | 17.10 | 19 | 7.82 ± 3.10 | 0.27 ± 0.08 | 111.39 ± 67.48 |
| 60 | 25.66 | 19 | 6.58 ± 3.03 | 0.25 ± 0.11 | 103.89 ± 53.47 |
| 120 | 51.31 | 11 | 5.88 ± 3.45 | 0.19 ± 0.12 | 81.41 ± 66.90 |

Example 5

Fibroblast Attachment and Proliferation

The attachment and proliferation of fibroblasts to bundles of fibrin threads were evaluated qualitatively at days 1 and 7 for the investigation of biocompatibility and the support of cell growth for applications in tissue regeneration. One day after cell seeding, fibroblasts attached readily to both the uncrosslinked and UV crosslinked fibrin threads as visualized with a viability stain. Furthermore, both supported more fibroblast attachment than polypropylene threads. On all three thread types, fibroblasts tended to align along the long axis of the threads and in the grooves between threads in the bundles. While most cells were viable, non-viable cells were occasionally visualized on all thread types. By 7 days, viable cells were visualized on all thread types including controls. However, while areas of the crosslinked fibrin threads maintained relatively constant viable cell quantities compared to day 1, uncrosslinked threads supported robust proliferation. Fibroblasts on uncrosslinked fibrin threads were completely confluent with sheets of cells spanning the length of the threads and filling gaps between threads. While non-viable cells could be distinguished on all thread types, UV crosslinked fibrin threads fluoresced moderately in the red wavelengths, making non-viable cells more difficult to view and image.

Example 6

Effect of Fibroblast Growth Factor-2 (FGF-2) on Fibroblast Attachment and Proliferation on Fibrin Microthreads The effect of FGF-2 on fibroblast attachment and proliferation on fibrin microthreads was analyzed in two ways. In the first method, soluble FGF-2 was added to cells cultured on fibrin microthreads. Fibroblasts were seeded on fibrin microthreads in serum-free medium according to the method described in Example 1, in the presence or absence of 100 ng/mL of FGF-2. Media was changed daily over a period of seven days. The mean migration distance on day 7 was statistically significantly greater than that observed in the absence of soluble FGF-2.

Figure 7:
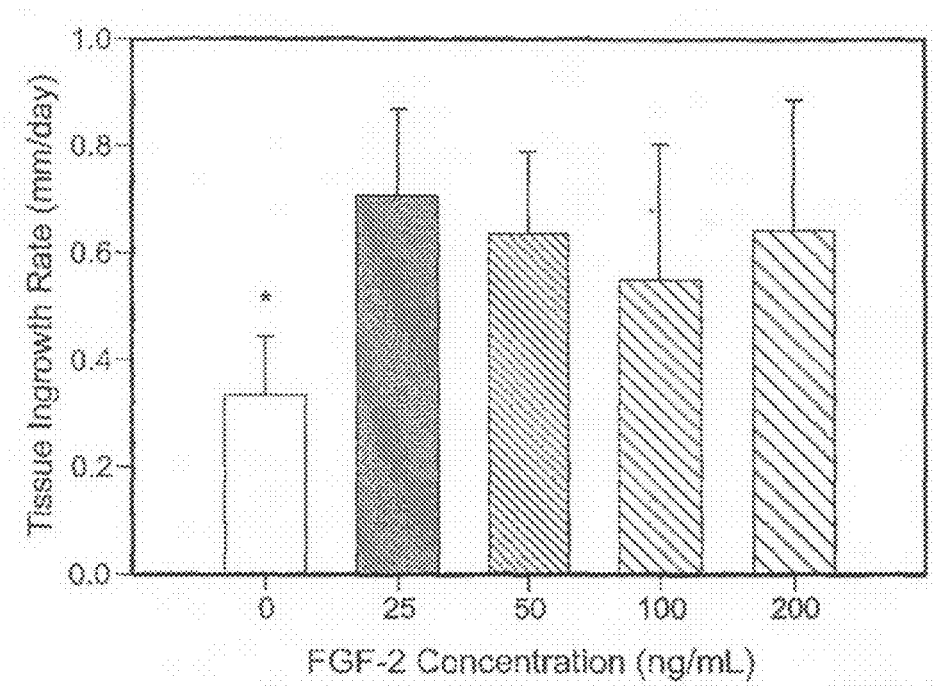
FIG. 7 depicts the results of an experiment analyzing the effect of FGF-2 on tissue ingrowth by fibroblasts cultured on fibrin microthreads.
Figure 8:
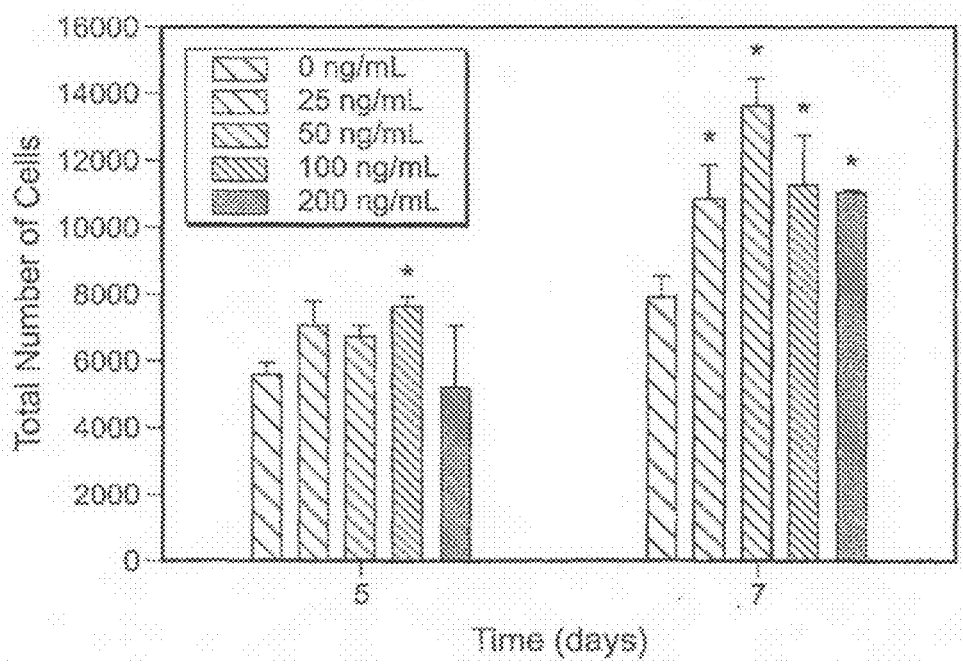
FIG. 8 depicts the results of an experiment analyzing the effect of FGF-2 on cell numbers of fibroblasts cultured on fibrin microthreads.

In the second method, FGF-2 was incorporated into fibrin microthreads during synthesis. Fibrin microthreads were prepared according to the method in Example 1, except that FGF-2 was added to the fibrinogen solution at a final concentration of 25, 50, 100 or 200 ng/mL. Cells were seeded according to the method described in Example 1 and tissue ingrowth rate (mm/day) and total cell numbers were measured over a period of seven days. Tissue ingrowth rate was increased in all FGF-2 containing fibrin microthreads, relative to the control fibrin micro threads, as shown in FIG. 7. Fibroblast proliferation was statistically significantly increased on day seven in the FGF-2 containing fibrin microthreads, relative to the control fibrin microthreads, as shown in FIG. 8.

A number of embodiments of the invention have been described. Nevertheless, it will be understood that various modifications may be made without departing from the spirit and scope of the invention. Accordingly, other embodiments are within the scope of the following claims.

What is claimed is:

1. A method of making a fibrin microthread, the method comprising:
   (a) combining a first volume of fibrinogen and a second volume of a molecule capable of forming fibrin from the fibrinogen to form a mixture;
   (b) transferring the mixture to a lumen containing device;
   (c) disposing a distal end of the lumen containing device into an aqueous bath;
   (d) moving the distal end of the lumen containing device through the aqueous bath at a first velocity;
   (e) extruding the mixture of the fibrinogen and the molecule through the distal end of the lumen containing device into an aqueous bath at a second velocity while moving the distal end of the lumen containing device through the aqueous bath at the first velocity, the second velocity being different than the first velocity;
   (f) allowing the fibrin microthread to substantially form in the aqueous bath.

2. The method of claim 1, wherein the fibrinogen is human fibrinogen or fibrinogen of a non-human primate, a domesticated animal, or a rodent.

3. The method of claim 1, wherein the fibrinogen is obtained from a naturally occurring source or is recombinantly produced.

4. The method of claim 1, wherein the molecule is a protease.

5. The method of claim 4, wherein the protease is thrombin.

6. The method of claim 1, further comprising recovering the fibrin microthread from the aqueous bath and permitting the fibrin microthread to dry.

7. The method of claim 1, further comprising providing a therapeutic agent and (a) extruding the therapeutic agent with the fibrinogen and the molecule thereby producing a fibrin microthread comprising the therapeutic agent or (b) associating the therapeutic agent with a formed fibrin microthread.

8. The method of claim 7, wherein the therapeutic agent is a growth factor, a protein, a chemotherapeutic agent, a vitamin, a mineral, an antimicrobial agent, a small organic molecule, or a biological cell.

9. The method of claim 8, wherein the growth factor is a cytokine or interleukin.

10. The method of claim 8, wherein the protein is a hormone, an extracellular matrix protein, or an antibody.

11. The method of claim 10, wherein the extracellular matrix protein is collagen, elastin, laminin, tenascin, or fibronectin.

12. The method of claim 8, wherein the antimicrobial agent is an antibacterial agent, an antiviral agent, an antifungal agent, or an antiparasitic agent.

13. The method of claim 1, further comprising the step of combining the fibrin microthread with a microthread comprising a non-fibrin polymer.

14. The method of claim 13, wherein the non-fibrin polymer is a synthetic polymer.

15. The method of claim 13, wherein the non-fibrin polymer is a natural polymer.

16. The method of claim 15, wherein the natural polymer comprises collagen or a collagen-based material, hyaluronic acid or a hyaluronic acid-based material, cellulose or a cellulose-based material, silk and combinations thereof.

17. The method of claim 1, further comprising the step of recovering the fibrin microthread from the aqueous bath and subsequently associating the fibrin microthread with a substrate.

18. The method of claim 17, wherein the substrate is a woven or non-woven mesh, a surgical pin, a surgical screw, a surgical plate, a physiologically acceptable patch, dressing, bandage, or a natural or mechanical valve.

19. A method of forming a fibrin microthread using a dispensing apparatus, the dispensing apparatus comprising a first reservoir containing fibrinogen, a second reservoir containing a molecule capable of forming fibrin from the fibrinogen, a blending connector fluidically coupled to the first reservoir and the second reservoir, and a lumen containing device fluidically coupled to the blending connector, the method comprising:
   transferring a first volume of fibrinogen from the first reservoir to the blending connector;
   transferring a second volume of the molecule capable of forming fibrin from the fibrinogen from the second reservoir to the blending connector;
   the first volume of fibrinogen and the second volume of the molecule forming a mixture in the blending connector;
   transferring the mixture from the blending connector to the lumen containing device;
   disposing a distal end of the lumen containing device in an aqueous bath;
   moving the distal end of the lumen containing device through the aqueous bath at a first velocity; and
   extruding the mixture from the distal end of the lumen containing device into the aqueous bath at a second velocity while moving the distal end of the lumen containing device through the aqueous bath, the ratio of the second velocity to the first velocity in the range of about 1.5 to about 6.

20. The method of claim 19, wherein the ratio of the second velocity to the first velocity is about 2.

21. The method of the claim 19, wherein an internal diameter of the lumen containing device is in the range of about 250 μm to about 1,000 μm.

22. The method of claim 19, wherein the aqueous bath is maintained at a temperature in the range of about 18 degrees Celsius to about 40 degrees Celsius.

23. The method of claim 19, further comprising;
   removing the fibrin microthread from the aqueous bath after a predetermined time; and
   drying the fibrin microthread.

24. A method of forming a fibrin microthread comprising:
   combining a first volume of fibrinogen and a second volume of a molecule capable of forming fibrin from the fibrinogen to form a mixture;
   transferring the mixture to a lumen containing device;
   disposing a distal end of the lumen containing device in an aqueous bath;
   moving the distal end of the lumen containing device through the aqueous bath at a first velocity while extruding the mixture from the distal end of the lumen containing device into the aqueous bath at a second velocity, the second velocity being different than the first velocity;
   incubating the mixture in the aqueous bath for a predetermined incubation time to form the fibrin microthread.

25. The method of claim 24, wherein the incubation time is at least about 1 minute.

26. The method of claim 25, wherein the incubation time is at least about 3.5 minutes.

27. The method of claim 24, wherein the incubation time is in the range of about 1 minutes to about 30 minutes.

28. The method of claim 1, wherein the fibrin microthread has a tensile strength of at least about 4 MPa.

* * * * *